(12) United States Patent  (10) Patent No.: US 7,629,473 B2
Kehler et al.  (45) Date of Patent: *Dec. 8, 2009

(54) 2-(1H-INDOLYLSULFANYL)-ARYL AMINE DERIVATIVES

(75) Inventors: Jan Kehler, Kgs. Lyngby (DK);
Karsten Juhl, Greve (DK); Morten Bang Norgaard, Lyngby (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 344 days.

This patent is subject to a terminal disclaimer.

(21) Appl. No.: 11/453,022

(22) Filed: Jun. 14, 2006

(65) Prior Publication Data

US 2006/0287382 A1    Dec. 21, 2006

Related U.S. Application Data

(60) Provisional application No. 60/692,009, filed on Jun. 17, 2005.

(30) Foreign Application Priority Data

Jun. 17, 2005    (DK) .............................. 2005 00894

(51) Int. Cl.
C07D 209/36  (2006.01)
A61K 31/40  (2006.01)
(52) U.S. Cl. ....................... 548/484; 514/418
(58) Field of Classification Search ............... 548/484; 514/418
See application file for complete search history.

(56) References Cited

U.S. PATENT DOCUMENTS

| | | | |
|---|---|---|---|
| 3,803,143 A | 4/1974 | Tanaka et al. |
| 4,018,830 A | 4/1977 | Christy et al. |
| 4,055,665 A | 10/1977 | Christy et al. |
| 4,056,632 A | 11/1977 | Mehta et al. |
| 4,198,417 A | 4/1980 | Ong et al. |
| 4,241,071 A | 12/1980 | Martin et al. |
| 5,095,039 A | 3/1992 | Mehta et al. |
| 5,945,425 A | 8/1999 | Moormann et al. |
| 6,410,736 B1 | 6/2002 | Howard et al. |
| 6,436,938 B1 | 8/2002 | Howard et al. |
| 6,455,738 B1 | 9/2002 | Dubac et al. |
| 6,509,340 B1 | 1/2003 | Van Amsterdam et al. |
| 6,596,741 B2 | 7/2003 | Howard et al. |
| 6,906,078 B2 | 6/2005 | Moorman et al. |
| 7,189,501 B2 | 3/2007 | Makuta et al. |
| 7,199,147 B2 | 4/2007 | Imazaki et al. |
| 7,217,732 B2 | 5/2007 | Kozlowski et al. |
| 7,229,751 B2 | 6/2007 | Kimura et al. |
| 7,247,651 B2 | 7/2007 | Madera et al. |
| 2002/0173524 A1 | 11/2002 | Collins et al. |
| 2003/0187023 A1 | 10/2003 | Kubo et al. |
| 2003/0207894 A1 | 11/2003 | Theodoridis et al. |
| 2004/0009959 A1 | 1/2004 | Potter et al. |
| 2004/0014774 A1 | 1/2004 | Myers et al. |
| 2004/0023010 A1 | 2/2004 | Bulovic et al. |
| 2004/0039035 A1 | 2/2004 | Collins et al. |
| 2004/0072844 A1 | 4/2004 | Madera et al. |
| 2004/0077854 A1 | 4/2004 | Halazy et al. |
| 2004/0132778 A1 | 7/2004 | Lacadie et al. |
| 2004/0137389 A1 | 7/2004 | Fukui et al. |
| 2004/0176426 A1 | 9/2004 | Houze et al. |
| 2004/0186148 A1 | 9/2004 | Shankar et al. |
| 2004/0192664 A1 | 9/2004 | Kunz et al. |
| 2004/0204451 A1 | 10/2004 | Lacadie et al. |
| 2004/0209936 A1 | 10/2004 | Bratton et al. |
| 2004/0220237 A1 | 11/2004 | Fu et al. |
| 2004/0266732 A1 | 12/2004 | Galvez et al. |
| 2005/0107599 A1 | 5/2005 | Makioka et al. |
| 2005/0123501 A1 | 6/2005 | Lewis |
| 2005/0136065 A1 | 6/2005 | Valiante, Jr. |
| 2005/0152859 A1 | 7/2005 | Dooley et al. |
| 2005/0153980 A1 | 7/2005 | Schadt, Jr. et al. |
| 2005/0159556 A1 | 7/2005 | Lewis et al. |
| 2005/0189519 A1 | 9/2005 | Gothe et al. |
| 2005/0206994 A1 | 9/2005 | Kokeguchi et al. |
| 2005/0228020 A1 | 10/2005 | Miyamoto et al. |
| 2005/0238992 A1 | 10/2005 | Kodama |
| 2005/0250794 A1 | 11/2005 | Napper et al. |
| 2005/0261298 A1 | 11/2005 | Solow-Cordero et al. |
| 2005/0282861 A1 | 12/2005 | Friary et al. |
| 2006/0030593 A1 | 2/2006 | Bernotas et al. |
| 2006/0069203 A1 | 3/2006 | Lewis et al. |

(Continued)

FOREIGN PATENT DOCUMENTS

EP    0 273 199 A2    7/1988

(Continued)

OTHER PUBLICATIONS

A. Burger, Isosterism and bioisosterism in drug design. Prog. Drug Res. 37 (1991), pp. 287-371).*

(Continued)

*Primary Examiner*—Rebecca L Anderson
*Assistant Examiner*—Robert Havlin
(74) *Attorney, Agent, or Firm*—Stephen G. Kalinchak; Margaret M. Buck

(57) ABSTRACT

The present invention relates to compounds of formula IV

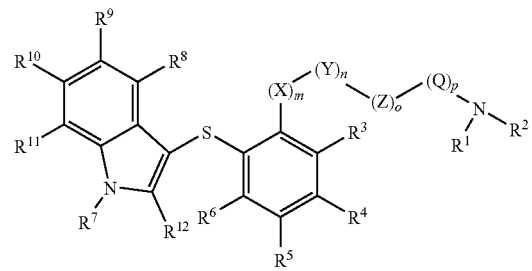

and their use.

18 Claims, No Drawings

U.S. PATENT DOCUMENTS

| | | |
|---|---|---|
| 2006/0135540 A1 | 6/2006 | Lin et al. |
| 2006/0141286 A1 | 6/2006 | Tada et al. |
| 2006/0148801 A1 | 7/2006 | Hsieh et al. |
| 2006/0216546 A1 | 9/2006 | Tada |
| 2006/0276440 A1 | 12/2006 | An et al. |
| 2006/0287386 A1 | 12/2006 | Kehler et al. |
| 2007/0004923 A1 | 1/2007 | Kobayashi et al. |
| 2007/0054904 A1 | 3/2007 | Knolle et al. |
| 2007/0060595 A1 | 3/2007 | Yoshizawa et al. |
| 2008/0176922 A1* | 8/2008 | Kehler et al. ............ 514/418 |

FOREIGN PATENT DOCUMENTS

| | | |
|---|---|---|
| EP | 0 396 827 A1 | 11/1990 |
| EP | 0 402 097 A1 | 12/1990 |
| EP | 0 755 923 A1 | 1/1997 |
| EP | 0 814 084 A1 | 12/1997 |
| EP | 0 921 124 A1 | 6/1999 |
| EP | 1 793 272 A1 | 6/2007 |
| WO | WO 93/11106 A1 | 6/1993 |
| WO | WO 93/12080 | 6/1993 |
| WO | WO 94/14770 A1 | 7/1994 |
| WO | WO 97/17325 | 5/1997 |
| WO | WO 97//17352 A1 | 5/1997 |
| WO | WO 97/48698 A1 | 12/1997 |
| WO | WO 98/08817 | 3/1998 |
| WO | WO 00/59878 | 10/2000 |
| WO | WO 00/66537 | 11/2000 |
| WO | WO 01/10842 A2 | 2/2001 |
| WO | WO 01/27068 A1 | 4/2001 |
| WO | WO 01/49677 A1 | 7/2001 |
| WO | WO 01/49678 A1 | 7/2001 |
| WO | WO 01/49679 A1 | 7/2001 |
| WO | WO 02/40024 A1 | 5/2002 |
| WO | WO 02/062766 A2 | 8/2002 |
| WO | WO 02/098857 A1 | 12/2002 |
| WO | WO 03/029232 A1 | 4/2003 |
| WO | WO 03/055873 A1 | 7/2003 |
| WO | WO 2005/061455 A1 | 7/2005 |
| WO | WO 2006/006172 A2 | 1/2006 |
| WO | WO 2006/007843 A1 | 1/2006 |
| WO | WO 2006/018850 A2 | 2/2006 |
| WO | WO 2006/038741 A1 | 4/2006 |
| WO | WO 2006/063606 A1 | 6/2006 |
| WO | WO 2006/098380 A1 | 9/2006 |

OTHER PUBLICATIONS

Jackson et al. (CAPLUS Abstract of: Journal of Chemical Research, Synopses (1988), (9), 272-3).*

Jackson, A., et al., "Electrophilic Substitution in Indoles Part 16: The Formation of Indolobenzothiazines and Indolobenzothiazepines by Intramolecular Cyclisation of (o-Nitrophenylthio)Indoles", J. Chem. Res. Miniprint, vol. 9, 1988, pp. 2017-2063.

Ragno, R., et al., "Docking and 3-D QSAR Studies on Indolyl Aryl Sulfones. Binding Mode Exploration at the HIV-1 Reverse Transcriptase Non-Nucleoside Binnding Site and Design of Highly Active N-(2-Hydroxyethyl)carboxamide and N-(2-hydroxyethyl)carbohydrazide Derivatives", J. Med. Chem., vol. 48. No. 1, 2005, pp. 213-223.

Silvestri, R., et al., "Novel Indolyl Aryl Sulfones Active Against HIV-1 Carrying NNRTI Resistance Mutations: Synthesis and SAR Studies", J. Med. Chem., vol. 46, 2003, pp. 2482-2493.

Edmond, P., et al. "Substituted Diphenyl Sulfides as Selective Serotonin Transporter Ligands: Synthesis and In Vitro Evaluation", J. Med. Chem., 2002, vol. 45, pp. 1253-1258.

Jilek, J., et al. "Potential Antidepressants: 2-(Methoxy- And Hydroxy-Phenylthio)Benzylamines As Selective Inhibitors Of 5-Hydroxytryptamine Re-uptake In the Brain", Collect. Czech. Chem. Commun., 1989, vol. 54, pp. 3294-3338.

Sindelar, K., et al. "Potential Antidepressants And Inhibitors Of 5-Hydroxy-Tryptamine And Noradrenaline Re-uptake In The Brain: N,N-Dimethyl-(Arylthio)Thenylamines And N,N-Dimethyl-2-(Thienylthio)Benzylamines", Collect. Czech. Chem. Commun., 1991, vol. 56, pp. 449-458.

Oya, S., et al. "A New Single-Photon Emission Computed Tomography Imaging Agent For Serotonin Transporters: [123I] IDAM, 5-iodo-2-((2-((dimethylamino)methyl)-phenyl)thio)benzyl Alcohol", J. Med. Chem., 1999, vol. 42(3), pp. 333-335.

Oya, S., et al. "New PET Imaging Agent for the Serotonin Transporter: [18F]ACF (2-[(2-Amino-4-chloro-5-fluorophenyl)thio]-N,N-dimethyl-benzenmethanamine)", J. Med. Chem., 2002, vol. 45, pp. 4716-4723.

Axford, L., et al. "Bicyclo[2.2.1]heptanes as Novel Triple Re-uptake Inhibitors for the Treatment of Depression" Bioorganic & Medicinal Chemistry Letters, 2003, pp. 3277-3280, vol. 13.

Hawkins, D.G., et al. "Competitive Cyclisation of Singlet and Triplet Nitrenes. Part 7. Reaction Pathways of 2-Azidophenyl Benzothienyl Azides", Journal of the Chemical Society, Perkin Transactions I: Organic and Bio-Organic Chemistry, 1979, pp. 3207-3210, No. 12.

Martin, L., et al. "Synthesis of Spiro[isobenzofuran-1(3H),4'piperedines] as potential Central Nervous System Agents. Conformationally Mobile Analogues Derived by Furan Ring Opening", J. Med. Chem., 1979, pp. 1347-1354, vol. 22, No. 11.

Abstract and STN Search Report cited in the Jul. 10, 2008 Office Action in connection with parallel U.S. Appl. No. 11/452,823.

Mitra, et al.; "Thiophenes & Thiapyrans: Part XVII—Thieno-(2:3-b)-thionaphtheno & Thionaphtheno-(2:3-b)-thionaphthene", Journal of Scientific & Industrial Research., 1957, 16B:348-54.

Sejberg, J. Synth[e]sis of 3- and 2-phenylsulfanyl-1H-indole [thesis] (English Translation). Lyngby (Denmark): Technical University of Denmark; Jan. 21, 2003. 102 pages (Tables 6, 7 and 8 are attached at the end of the document). Available from: Technical University of Denmark, Lyngby, DK; d991811.

Wong, D. T. "Duloxetine (LY 248686): an inhibitor of Serotonin and noradrenaline uptake and antidepressant drug candidate" Exp. Opin. Invest. Drugs, 1998, 7(10), 1691-1699.

Khan, et al. "Venlafaxine in Depressed Outpatients" Psychopharmacology Bulletin, 1991, 27, 141-144.

Katzman, M. "Venlafaxine in the Treatment of Anxiety Disorders" Expert Rev. Neurotherapeutics, 2004, 4(3), 371-381.

NME Drug and New Biologic Approvals in 2004 [online] retrieved on Jun. 4, 2009; retrieved from the Internet [URL; http:www.fda.gov/Drugs/DevelopmentApprovalProcess/HowDrugsareDevelopedandApproved/DrugandBiotogicApprovalReports/NMEDrugandNewBiologicApprovals/ucm081677.htm].

May 20, 2008 NDA Approval Letter [online] retrieved on Jun. 4, 2009; retrieved from the Internet [URL; http://www.accessdata.fda.gov/drugsatfda_docs/appletter/2008/022104s000ltr.pdf].

Berk, M. "Duloxetine: A review" Expert Rev. Neurotherapeutics, 2003, 3(4), 447-451.

Fishbain, et al. "Evidence-Based Data From Animal and Human Experimental Studies on Pain Relief with Anti-depressants: A Structural Review" Pain Medicine, 2000, 1(4), 310-316.

CDER New Molecular Entity (NME) Drug and New Biologic Approvals for Calendar Year 2009 (Updated through Apr. 30, 2009) [online] retrieved on Jun. 4, 2009; retrieved from the Internet [URL: http:www.fda.gov/downloads/Drugs/DevelopmentApprovalProcess/HowDrugsareDevelopedandApproved/DrugandBiologicApprovalReports/NMEDrugandNewBiologicApprovals/UCM091095.pdf].

Mukaddes, et al. "Venlafaxine in Attention Deficit Hyperactivity Disorder" European Neurophyschopharmacology, 2002, 12, supplement 3, p. 421.

Dmochowski, et al. "Duloxetine Versus Placebo for the Treatment of North American Women with Stress Urinary Incontinence." The Journal of Urology, 2003, 170, 1259-1263.

Depressed Mood [online] retrieved on Dec. 2, 2008; retrieved from the Internet [URL; http://www.healthline.com/adamcontent/depresion].

Fibromyalgia [online] retrieved on Dec. 2, 2008; retrieved from the Internet [URL; http://www.nlm.nih.gov/medlineplus/ency/article/000427.htm].

Obsessive-compulsive disorder [online] retrieved on Dec. 2, 2008; retrieved from the Internet [URL; http://www.nlm.nih.gov/medlineplus/ency/article/000929.htm].

* cited by examiner

2-(1H-INDOLYLSULFANYL)-ARYL AMINE DERIVATIVES

This application claims priority under 35 U.S.C. § 119(e) of U.S. Provisional Application No. 60/692,009 filed Jun. 17, 2005, and claims foreign priority under 35 U.S.C. § 119(a)-(d) of Danish Patent Application No. PA200500894, filed Jun. 17, 2005, the contents of which are hereby incorporated by reference into the subject application.

FIELD OF THE INVENTION

The present invention relates to compounds of formula IV and the medical use thereof e.g. in the treatment of affective disorders, pain disorders, attention deficit hyperactivity disorder (ADHD) and stress urinary incontinence.

BACKGROUND OF THE INVENTION

The majority of currently available antidepressants can be classified in 3 classes:
1) monoamine oxidase inhibitors (MAOIs),
2) biogenic amine neurotransmitter [serotonin (5-HT), norepinephrine (NE) and dopamine (DA)] transporter reuptake blockers, and
3) modulators, especially blockers of one or more of the 5-HT and/or NE receptors.

Since depression is associated with a relative deficiency of the biogenic amines, the use of 5-HT and/or NE-receptor blockers (i.e. 5-HT and or NE-antagonist's) have not proven very successful in the treatment of depression and anxiety and the preferred and currently most efficacious treatments are based on the enhancement of 5-HT and/or NE neurotransmission by blocking their reuptake back from the synaptic cleft (Slattery, D. A. et al., "The evolution of antidepressant mechanisms", *fundamental and Clinical pharmacology*, 2004, 18, 1-21; Schloss, P. et al, "new insights into the mechanism of antidepressant therapy", *Pharmacology and therapeutics*, 2004, 102, 47-60).

Selective serotonin reuptake inhibitors (hereinafter referred to as SSRIs) have become first choice therapeutics in the treatment of depression, certain forms of anxiety and social phobias, because they generally are effective, well tolerated and have a favourable safety profile compared to the classic tricyclic antidepressants. Drugs claimed to be SSRIs are for example fluoxetine, sertraline and paroxetine.

However, clinical studies on depression indicate that non-response to the known SSRIs is substantial, up to 30%. Another, often neglected, factor in the treatment of depression is the delay in the onset of the therapeutic effect of the SSRIs. Sometimes symptoms even worsen during the first weeks of treatment. Furthermore, sexual dysfunction is generally a side effect common to SSRIs. Accordingly, there is a desire for the development of compounds capable of improving the treatment of depression and other diseases related to malfunctioning of serotonin.

Dual re-uptake inhibitors providing the combined effect of 5-HT reuptake inhibition and NE (norepinephrine is also named noradrenaline, NA) reuptake inhibition on depression is explored in clinical studies of compounds such as Duloxetine (Wong, "Duloxetine (LY-248686): an inhibitor of serotonin and noradrenaline uptake and an antidepressant drug candidate", *Expert Opinion on Investigational Drugs*, 1998, 7, 10, 1691-1699) and Venlafaxine (Khan-A et al, 30 "Venlafaxine in depressed outpatients", *Psychopharmacology Bulletin*, 1991, 27, 141-144). Compounds having such dual effect are also named SNRIs, "serotonin and noradrenaline reuptake inhibitors", or NSRIs, "noradrenaline and serotonin reuptake inhibitors".

Since treatment with the selective NE reuptake inhibitor reboxetine has been shown to stimulate 5-HT neurons and mediate the release of 5-HT in the brain (Svensson, T. et al, *J. Neural. Transmission*, 2004, 111, 127) there might be a synergistic advantage using SNRI's in the treatment of depression or anxiety.

The use of SNRI's have been shown in clinical studies to have a beneficial effect on pain (e.g. Fibromyalgia syndrome, overall pain, back pain, shoulder pain, headache, pain while awake and during daily activities) and especially pain associated with depression (Berk, M. *Expert Rev. Neurotherapeutics* 2003, 3, 47-451; Fishbain, D. A., et al. "Evidence-based data from animal and human experimental studies on pain relief with antidepressants: A structured review" Pain Medicine 2000 1: 310-316).

SNRI's have also been shown in clinical studies to have a beneficial effect in attention deficit hyperactivity disorder (ADHD) (N. M. Mukaddes; Venlafaxine in attention deficit hyperactivity disorder, European Neuropsychopharmacology, Volume 12, Supplement 3, October 2002, Page 421).

Furthermore, SNRI's have been shown to be effective for the treatment of stress urinary incontinence (Dmochowski R. R. et al. "Duloxetine versus placebo for the treatment of North American women with stress urinary incontinence", Journal of Urology 2003, 170: 4, 1259-1263.)

Naranjo, C. et al. "The role of the brain reward system in depression" *Prog. Neuro-Psychopharmacol. Biol. Psychiatry* 2001, 25, 781-823 discloses clinical and preclinical findings of links between lack of extra cellular dopamine in the mesocorticolimbic system and anhedonia, which is one of the main symptoms of depression.

Wellbutrin (bupropion) which has DA re-uptake activity in vitro and in vivo, shows antidepressant efficacy. Other combination studies have indicated that addition of some affinity at the DA uptake site may have some clinical benefit (Nelson, J. C. J. *Clin. Psychiatry* 1998, 59, 65; Masand, P. S. et al. *Depression Anxiety* 1998, 7, 89; Bodkin, J. A et al. *J. Clin. Psychiatry* 1997, 58, 137).

Axford L. et al. (2003, *Bioorganic & Medical Chemistry Letters*, 13, 3277-3280: "Bicyclo[2.2.1.]heptanes as novel triple re-uptake inhibitors for the treatment of depression") describe the development of triple 5-HT, NE and DA re-uptake inhibitors for treatment of depression. The combination of an SSRI and a norepinephrine and dopamine reuptake inhibitor, has been shown to have better efficacy in SSRI-non-responders (Lam R. W. et al. "Citalopram and Bupropion-SR: Combining Versus Switching in Patients With Treatment-Resistant Depression." *J. Clin. Psychiatry* 2004, 65, 337-340).

There is clinical evidence suggesting the combination of an SSRI and a norepinephrine and dopamine reuptake inhibitor induces less sexual dysfunction, than treatment with SSRI's alone (Kennedy S. H. et al. "Combining Bupropion SR With Venlafaxine, Paroxetine, or Duloxetine: A Preliminary Report on Pharmacokinetic, Therapeutic, and Sexual Dysfunction Effects" *J. Clin. Psychiatry* 2002, 63, 181-186).

Diphenyl sulphides of formula I and variations thereof have been disclosed as serotonin re-uptake inhibitors and have been suggested for use in treatment of depression, cf. e.g. WO03029232(A1).

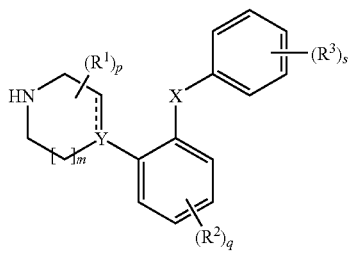

formula I

Diphenyl sulphides of formula II and variations thereof have been disclosed as serotonin re-uptake inhibitors and have been suggested for use in treatment of depression, cf. e.g. U.S. Pat. No. 5,095,039, U.S. Pat. No. 4,056,632, EP 396827 A1 and WO 9312080. EP 402097 describes halogen substituted diphenylsulfides claimed to be selective serotonin inhibitors for treatment of depression. Likewise WO 9717325 disclose derivatives of N,N-dimethyl-2-(arylthio)benzylamine claimed to be selective serotonin transport inhibitors and suggest their use as antidepressants. J. Jilek et al., *Collect. Czeck Chem. Commun.* 1989, 54, 3294-3338 also discloses various derivatives of diphenyl sulphides, "phenyl-thio-benzylamines" as antidepressants. Furthermore, diphenyl sulphides are also disclosed in U.S. Pat. No. 3,803,143 and claimed useful as antidepressant.

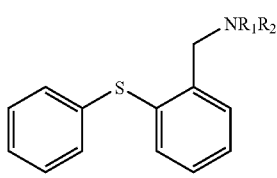

formula II

K. Sindelar et al., (K. Sindelar et al. *Collect. Czeck Chem. Commun.* 1991, 56, 449-458) disclose compounds of formula III with test for selectivity as 5-HT re-uptake inhibitor and NA re-uptake inhibitor, respectively, for use as antidepressants.

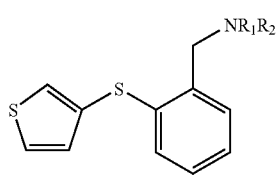

formula III

The above-mentioned references do not disclose compounds comprising an indole group like the indolyl-sulfanyl arylamines of the present invention.

The present invention provides 2-(1H-indolylsulfanyl)-aryl amine derivatives of formula IV which are serotonin reuptake inhibitors. A particular aspect of the invention provides compounds possessing the combined effect of serotonin reuptake inhibition and norepinephrine reuptake inhibition. Another particular aspect of the invention provides compounds possessing the combined effect of serotonin reuptake inhibition and dopamine reuptake inhibition. Furthermore, some of the compounds are also triple 5-HT, NE and DA re-uptake inhibitors.

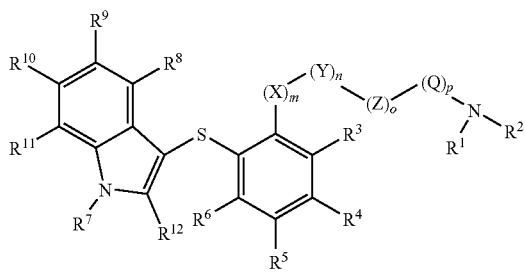

formula IV wherein X, Y, Z, Q, m, n, o, p and $R^1$-$R^{12}$ are as defined below.

SUMMARY OF THE INVENTION

One object of the invention is the provision of compounds, which are serotonin reuptake inhibitors. Another object of the invention is the provision of compounds, which are both serotonin reuptake inhibitors and noradrenaline reuptake inhibitors. Yet another object of the invention is the provision of compounds, which are both serotonin reuptake inhibitors and dopamine reuptake inhibitors. Yet another object of the invention is the provision of compounds, which are serotonin reuptake inhibitors, noradrenaline reuptake inhibitors and dopamine reuptake inhibitors.

The compounds of the invention are substituted indole derivatives of the general formula IV as the free base or salts thereof.

The invention provides a compound according to the above for use as a medicament.

The invention provides a pharmaceutical composition comprising a compound according to the above and at least one pharmaceutically acceptable carrier or diluent.

The invention provides the use of a compound according to the above for the preparation of a pharmaceutical composition for the treatment of affective disorders, pain disorders, ADHD and stress urinary incontinence.

The invention furthermore concerns the use of a compound according to the above in a method of treatment of affective disorders, pain disorders, ADHD and stress urinary incontinence.

Definition of Substituents

The term heteroatom refers to a nitrogen, oxygen or sulphur atom.

Halo means halogen. Halogen means fluoro, chloro, bromo or iodo.

The expression "$C_{1-6}$-alk(en/yn)yl" means a $C_{1-6}$-alkyl, a $C_{2-6}$-alkenyl or a $C_{2-6}$-alkynyl group. The term "$C_{1-6}$-alkyl" refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl. The term "$C_{2-6}$-alkenyl" refers to a branched or unbranched alkenyl group having from two to six carbon atoms, including one double bond, including but not limited to ethenyl, propenyl, and butenyl. The term "$C_{2-6}$-alkynyl" refers to a branched or unbranched alkynyl group having from two to six carbon atoms, including one triple bond, including but not limited to ethynyl, propynyl and butynyl.

The expression "$C_{3-8}$-cycloalk(en)yl" means a $C_{3-8}$-cycloalkyl or a $C_{3-8}$-cycloalkenyl group. The term "$C_{3-8}$-cycloalkyl" designates a monocyclic or bicyclic carbocycle having three to eight C-atoms, including but not limited to cyclopropyl, cyclopentyl, and cyclohexyl. The term "$C_{3-8}$-cycloalkenyl" designates a monocyclic or bicyclic carbocycle having three to eight C-atoms and one double bond, including but not limited to cyclopropenyl, cyclopentenyl and cyclohexenyl.

In the expression "$C_{3-8}$-cycloalk(en)yl-$C_{1-6}$-alk(en/yn)yl", "$C_{1-6}$-alk(en/yn)ylamino", "di-($C_{1-6}$-alk(en/yn)yl)amino", "$C_{1-6}$-alk(en/yn)ylcarbonyl", "$C_{1-6}$-alk(en/yn)ylaminocarbonyl", "di-($C_{1-6}$-alk(en)yl)aminocarbonyl", "$C_{1-6}$-alk(en/yn)yloxy", "$C_{1-6}$-alk(en/yn)ylsulfanyl", "halo-$C_{1-6}$-alk(en/yn)yl", "halo-$C_{1-6}$-alk(en/yn)ylsulfonyl", "halo-$C_{1-6}$-alk(en/yn)ylsulfanyl" and "$C_{1-6}$-alk(en/yn)ylsulfonyl" the terms "amino", "$C_{3-8}$-cycloalk(en)yl", "$C_{1-6}$-alk(en/yn)yl", "$C_{1-6}$-alk(en)yl" and "halo" are as defined above.

The term "aminocarbonyl" designates $NH_2—C=O$ which is attached to the remainder of the molecule via the carbon atom.

The term "$R^1$ and $R^2$ together with the nitrogen form a 4-7 membered ring containing zero or one double bond, optionally said ring in addition to said nitrogen comprises one further heteroatom selected from oxygen and sulphur" refers to such ring systems wherein a ring is formed by the nitrogen to which $R^1$ and $R^2$ are attached and 3-6 atoms selected from 2-6 carbonatoms and 0-1 heteroatoms selected from sulphur and oxygen, said ring contains zero or one double bond. Examples of rings formed by $R^1$, $R^2$ and the nitrogen to which they are attached are pyrrolidine, piperidine, morpholine and thiomorpholine.

DESCRIPTION OF THE INVENTION

The present invention relates to a compound represented by the general formula IV

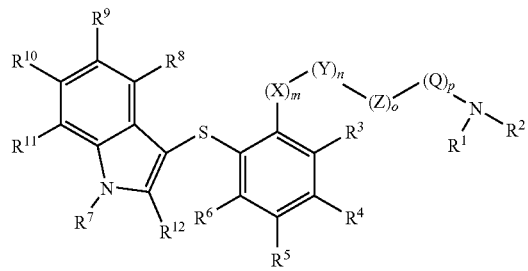

formula IV wherein $R^1$—$R^2$ are independently selected from hydrogen, $C_{1-6}$-alk(en/yn)yl, $C_{3-8}$-cycloalk(en)yl, and $C_{3-8}$-cycloalk(en)yl-$C_{1-6}$-alk(en/yn)yl; or $R^1$ and $R^2$ together with the nitrogen form a 4-7 membered ring containing zero or one double bond, optionally said ring in addition to said nitrogen comprises one further heteroatom selected from oxygen and sulphur;

$R^3$—$R^6$ and $R^8$-$R^{12}$ are independently selected from hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en/yn)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl;

$R^7$ is selected from hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

X is selected from the group consisting of $CH_2$, $CHR^{13}$ or $CR^{14}R^{15}$;

Y is selected from the group consisting of $CH_2$, $CHR^{16}$ and $CR^{17}R^{18}$;

Z is selected from the group consisting of $CH_2$, $CHR^{19}$ and $CR^{20}R^{21}$; and Q is selected from the group consisting of $CH_2$, $CHR^{22}$ and $CR^{23}R^{24}$;

m, n, o and p are independently 0 or 1 with the proviso that when m+n+o+p equals to 1 then none of X, Y, Z and Q are $CH_2$;

wherein $R^{13}$—$R^{24}$ are independently selected from the group consisting of $C_{1-6}$-alk(en/yn)yl, $C_{3-8}$-cycloalk(en)yl and $C_{3-8}$-cycloalk(en)yl-$C_{1-6}$-alk(en/yn)yl;

as the free base or a salt thereof.

In one embodiment of the compound of formula IV, $R^1$ and $R^2$ are independently selected from the group consisting of $C_{3-8}$-cycloalk(en)yl and $C_{3-8}$-cycloalk(en)yl-$C_{1-6}$-alk(en/yn)yl. In a further embodiment of the compound of formula IV, $R^1$ and $R^2$ are independently selected from the group consisting of hydrogen and $C_{1-6}$-alk(en/yn)yl; or $R^1$ and $R^2$ together with the nitrogen form a 4-7 membered ring containing zero or one double bond, optionally said ring in addition to said nitrogen comprises one further heteroatom selected from oxygen and sulphur.

To further illustrate without limiting the invention an embodiment of $R^1$ is hydrogen; another embodiment of $R^1$ is $C_{1-6}$-alk(en/yn)yl such as methyl.

To further illustrate without limiting the invention an embodiment of $R^2$ is hydrogen; another embodiment of $R^2$ is $C_{1-6}$-alk(en/yn)yl such as methyl.

To further illustrate without limiting the invention, an embodiment of the compound of formula IV concerns such compounds wherein $R^1$ and $R^2$ together with the nitrogen form a 4-7 membered ring containing zero or one double bond, optionally said ring in addition to said nitrogen comprises one further heteroatom selected from oxygen and sulphur. In one embodiment said 4-7 membered ring does not contain any double bond; in another embodiment said 4-7 membered ring does contain one double bond. In one embodiment the only heteroatom contained in said 4-7 membered ring is the nitrogen to which $R^1$ and $R^2$ are attached. In another embodiment said 4-7 membered ring contains one heteroatom in addition to the nitrogen to which $R^1$ and $R^2$ are attached; in a further embodiment said heteroatom is sulphur; in a further embodiment said heteroatom is oxygen. Typically said 4-7 membered ring is selected from the group consisting of morpholine and thiomorpholine.

In a further embodiment of the compound of formula IV, $R^3$—$R^6$ and $R^8$—$R^{12}$ are independently selected from the group consisting of $C_{1-6}$-alk(en/yn)ylcarbonyl, aminocarbonyl, $C_{1-6}$-alk(en/yn)ylaminocarbonyl, di-($C_{1-6}$-alk(en/yn)yl)aminocarbonyl and hydroxy.

In a further embodiment of the compound of formula IV, $R^3$—$R^6$ and $R^8$—$R^{12}$ are independently selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, amino, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl In a further embodiment of the compound of formula IV, $R^3$—$R^6$ and $R^8$—$R^{12}$ are independently selected from the group consisting of hydrogen, halogen, nitro, $C_{1-6}$-alk(en/yn)yl, di-($C_{1-6}$-alk(en/yn)yl)amino, $C_{1-6}$-alk(en/yn)yloxy and $C_{1-6}$-alk(en/yn)ylsulfonyl.

In a further embodiment of the compound of formula IV, $R^3$—$R^6$ and $R^8$—$R^{12}$ are independently selected from the group consisting of hydrogen, halogen, $C_{1-6}$-alk(en/yn)yl, and $C_{1-6}$-alk(en/yn)yloxy.

In an embodiment of the compound of formula IV, $R^3$—$R^6$ are independently selected from the group consisting of nitro, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en/yn)yl)aminocarbonyl, hydroxy, halo-$C_{1-6}$-alk(en/yn)ylsulfonyl and $C_{1-6}$-alk(en/yn)ylsulfonyl.

In a further embodiment of the compound of formula IV, $R^3$—$R^6$ are independently selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, $C_{1-6}$-alk(en/yn)yloxy, $C_{1-6}$-alk(en/yn)ylsulfanyl and halo-$C_{1-6}$-alk(en/yn)ylsulfanyl.

Typically, $R^3$—$R^6$ are independently selected from the group consisting of hydrogen, halogen and $C_{1-6}$-alk(en/yn)yloxy.

To further illustrate without limiting the invention an embodiment of $R^3$ is hydrogen.

Typically, $R^4$ is selected from the group consisting of hydrogen, halogen and $C_{1-6}$-alk(en/yn)yloxy. To further illustrate without limiting the invention an embodiment of $R^4$ is hydrogen; another embodiment of $R^4$ is halogen such as chloro or fluoro; another embodiment of $R^4$ is $C_{1-6}$-alk(en/yn)yloxy such as methoxy.

Typically, $R^5$ is selected from the group consisting of hydrogen and $C_{1-6}$-alk(en/yn)yloxy.

To further illustrate without limiting the invention an embodiment of $R^5$ is hydrogen; another embodiment of $R^5$ is $C_{1-6}$-alk(en/yn)yloxy such as methoxy.

To further illustrate without limiting the invention an embodiment of $R^6$ is hydrogen.

In a further embodiment of the compound of formula IV, $R^8$—$R^{12}$ are independently selected from the group consisting of $C_{1-6}$-alk(en/yn)ylcarbonyl, aminocarbonyl, $C_{1-6}$-alk(en/yn)ylaminocarbonyl, di-($C_{1-6}$-alk(en/yn)yl)aminocarbonyl and hydroxy. In a further embodiment of the compound of formula IV, $R^8$—$R^{12}$ are independently selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfanyl, halo-$C_{1-6}$-alk(en/yn)ylsulfanyl and $C_{1-6}$-alk(en/yn)ylsulfonyl;

Typically, $R^8$—$R^{12}$ are independently selected from the group consisting of hydrogen, halogen, nitro, $C_{1-6}$-alk(en/yn)yl, di-($C_{1-6}$-alk(en/yn)yl)amino, $C_{1-6}$-alk(en/yn)yloxy and $C_{1-6}$-alk(en/yn)ylsulfonyl.

In a further embodiment of the compound of formula IV, $R^8$—$R^{12}$ are independently selected from the group consisting of hydrogen, halogen, $C_{1-6}$-alk(en/yn)yl and $C_{1-6}$-alk(en/yn)yloxy.

Typically, $R^8$ is selected from the group consisting of hydrogen, halogen and $C_{1-6}$-alk(en/yn)yloxy. To further illustrate without limiting the invention an embodiment of $R^8$ is hydrogen; another embodiment of $R^8$ is halogen such as chloro or fluoro; another embodiment of $R^8$ is $C_{1-6}$-alk(en/yn)yloxy such as methoxy.

Typically, $R^9$ is selected from the group consisting of hydrogen, halogen, $C_{1-6}$-alk(en/yn)yl and di-($C_{1-6}$-alk(en/yn)yl)amino. To further illustrate without limiting the invention an embodiment of $R^9$ is hydrogen; another embodiment of $R^9$ is halogen such as chloro or fluoro; another embodiment of $R^9$ is $C_{1-6}$-alk(en/yn)yl such as methyl; another embodiment of $R^9$ is di-($C_{1-6}$-alk(en/yn)yl)amino such as dimethylamino.

Typically, $R^{10}$ is selected from the group consisting of hydrogen, halogen and $C_{1-6}$-alk(en/yn)ylsulfonyl. To further illustrate without limiting the invention an embodiment of $R^{10}$ is hydrogen; another embodiment of $R^{10}$ is halogen such as fluoro; another embodiment of $R^{10}$ is $C_{1-6}$-alk(en/yn)ylsulfonyl such as methylsulfonyl.

Typically, $R^{11}$ is selected from the group consisting of hydrogen, halogen, nitro and $C_{1-6}$-alk(en/yn)yloxy. To further illustrate without limiting the invention an embodiment of $R^{11}$ is hydrogen; another embodiment of $R^{11}$ is halogen such as chloro or fluoro; another embodiment of $R^{11}$ is nitro; another embodiment of $R^{11}$ is $C_{1-6}$-alk(en/yn)yloxy such as methoxy.

Typically, $R^{12}$ is selected from the group consisting of hydrogen and $C_{1-6}$-alk(en/yn)yl. To further illustrate without limiting the invention an embodiment of $R^{12}$ is hydrogen; another embodiment of $R^{12}$ is $C_{1-6}$-alk(en/yn)yl such as methyl.

In a further embodiment of the compound of formula IV, $R^7$ is selected from the group consisting of $C_{3-8}$-cycloalk(en)yl and $C_{3-8}$-cycloalk(en)yl-$C_{1-6}$-alk(en/yn)yl.

Typically, $R^7$ is selected from the group consisting of hydrogen and $C_{1-6}$-alk(en/yn)yl. To further illustrate without limiting the invention an embodiment of $R^7$ is hydrogen; another embodiment of $R^{12}$ is $C_{1-6}$-alk(en/yn)yl such as methyl.

In a further embodiment of the compound of formula IV, X is selected from the group consisting of $CHR^{13}$ and $CR^{14}R^{15}$, Y is selected from the group consisting of $CHR^{16}$ and $CR^{17}R^{18}$, Z is selected from the group consisting of $CHR^{19}$ and $CR^{20}R^{21}$, and Q is selected from the group consisting of $CHR^{22}$ and $CR^{23}R^{24}$.

In a further embodiment of the compound of formula IV, X, Y, Z and Q are $CH_2$.

In a further embodiment of the compound of formula IV, m+n+o+p equals to 1, 2, 3 or 4; in another embodiment of formula IV, m+n+o+p equals to 1; in another embodiment of formula IV, m+n+o+p equals to 2; in another embodiment of formula IV, m+n+o+p equals to 3; in another embodiment of formula IV, m+n+o+p equals to 4.

In a further embodiment of the compound of formula IV said compound is selected from the following list of compounds:

| Compound No | Name |
| --- | --- |
| 1 | {2-[5-Fluoro-2-(1H-indol-3-ylsulfanyl)-phenyl]-ethyl}-methyl-amine |
| 2 | {2-[2-(6-Fluoro-1H-indol-3-ylsulfanyl)-phenyl]-ethyl}-methyl-amine |
| 3 | {2-[2-(5-Fluoro-1H-indol-3-ylsulfanyl)-phenyl]-ethyl}-methyl-amine |
| 4 | {2-[2-(4-Fluoro-1H-indol-3-ylsulfanyl)-phenyl]-ethyl}-methyl-amine |
| 5 | {2-[2-(7-Fluoro-1H-indol-3-ylsulfanyl)-phenyl]-ethyl}-methyl-amine |
| 6 | {2-[2-(7-Methoxy-1H-indol-3-ylsulfanyl)-phenyl]-ethyl}-methyl-amine |
| 7 | {2-[2-(5-Fluoro-2-methyl-1H-indol-3-ylsulfanyl)-phenyl]-ethyl}-methyl-amine |
| 8 | {2-[2-(5-Chloro-1H-indol-3-ylsulfanyl)-phenyl]-ethyl}-methyl-amine |
| 9 | {2-[2-(4-Chloro-1H-indol-3-ylsulfanyl)-phenyl]-ethyl}-methyl-amine |
| 10 | {2-[2-(7-Chloro-1H-indol-3-ylsulfanyl)-phenyl]-ethyl}-methyl-amine |
| 11 | {2-[2-(1H-Indol-3-ylsulfanyl)-phenyl]-ethyl}-methyl-amine |
| 12 | {2-[2-(1-Methyl-indol-3-ylsulfanyl)-phenyl]-ethyl}-methyl-amine |
| 13 | {2-[5-Chloro-2-(1H-indol-3-ylsulfanyl)-phenyl]-ethyl}-methyl-amine |
| 14 | {2-[5-Chloro-2-(6-fluoro-1H-indol-3-ylsulfanyl)-phenyl]-ethyl}-methyl-amine |
| 15 | {2-[5-Chloro-2-(4-chloro-1H-indol-3-ylsulfanyl)-phenyl]-ethyl}-methyl-amine |
| 16 | {2-[5-Fluoro-2-(6-fluoro-1H-indol-3-ylsulfanyl)-phenyl]-ethyl}-methyl-amine |
| 17 | (2-(2-(4-Chloro-1H-indol-3-ylsulfanyl)-5-fluoro-phenyl)-ethyl)-methyl-amine |
| 18 | {2-[2-(6-Fluoro-1H-indol-3-ylsulfanyl)-4,5-dimethoxy-phenyl]-ethyl}-methyl-amine |
| 19 | {2-[2-(4-Chloro-1H-indol-3-ylsulfanyl)-4,5-dimethoxy-phenyl]-ethyl}-methyl-amine |
| 20 | {2-[2-(1H-Indol-3-ylsulfanyl)-4,5-dimethoxy-phenyl]-ethyl}-methyl-amine |
| 21 | {4-[2-(1H-Indol-3-ylsulfanyl)-phenyl]-butyl}-methyl-amine |
| 22 | {4-[2-(4-Methoxy-1H-indol-3-ylsulfanyl)-phenyl]-butyl}-methyl-amine |
| 23 | {4-[2-(4-Chloro-1H-indol-3-ylsulfanyl)-phenyl]-butyl}-methyl-amine |
| 24 | Methyl-{4-[2-(1-methyl-1H-indol-3-ylsulfanyl)-phenyl]-butyl}-amine |
| 25 | {3-[2-(4-Chloro-1H-indol-3-ylsulfanyl)-phenyl]-propyl}-methyl-amine |
| 26 | {3-[2-(4-Methoxy-1H-indol-3-ylsulfanyl)-phenyl]-propyl}-methyl-amine |
| 27 | Dimethyl-{3-[2-(3-methylamino-propyl)-phenylsulfanyl]-1H-indol-5-yl}-amine |
| 28 | Methyl-{3-[2-(7-nitro-1H-indol-3-ylsulfanyl)-phenyl]-propyl}-amine |
| 29 | {3-[2-(6-Methanesulfonyl-1H-indol-3-ylsulfanyl)-phenyl]-propyl}-methyl-amine |
| 30 | {3-[2-(1H-Indol-3-ylsulfanyl)-phenyl]-propyl}-methyl-amine |
| 31 | {3-[2-(6-Fluoro-1H-indol-3-ylsulfanyl)-phenyl]-propyl}-methyl-amine |
| 32 | Methyl-{3-[2-(1-methyl-1H-indol-3-ylsulfanyl)-phenyl]-propyl}-amine |
| 33 | Methyl-{3-[2-(5-methyl-1H-indol-3-ylsulfanyl)-phenyl]-propyl}-amine |
| 34 | 2-[2-(1H-Indol-3-ylsulfanyl)-phenyl]-ethylamine |
| 35 | {2-[2-(1H-Indol-3-ylsulfanyl)-phenyl]-ethyl}-dimethyl-amine |
| 36 | 3-[2-(2-Morpholin-4-yl-ethyl)-phenylsulfanyl]-1H-indole |
| 37 | 3-[2-(2-Thiomorpholin-4-yl-ethyl)-phenylsulfanyl]-1H-indole | as the free base or a salt thereof. Each of these compounds is considered a specific embodiment and may be subjected to individual claims.

The present invention comprises the free base and salts of the compounds of the invention, typically, pharmaceutically acceptable salts. The salts of the invention include acid addition salts, metal salts, ammonium and alkylated ammonium salts.

The salts of the invention are preferably acid addition salts. The acid addition salts of the invention are preferably pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-alotheophyllines, for example 8-bromotheophylline and the like. Further examples of pharmaceutical acceptable inorganic or organic acid addition salts include the pharmaceutically acceptable salts listed in *J. Pharm. Sci.* 1977, 66, 2, which is incorporated herein by reference.

Also intended as acid addition salts are the hydrates, which the present compounds are able to form.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centre and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials, or by stereoselective synthesis.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula IV which are readily convertible in vivo into the required compound of the formula IV. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Some compounds according to the invention inhibit the serotonin transporter and are thus serotonin reuptake inhibitors. Typically, the compounds have an in vitro uptake inhibition (IC50) of 5 µM or less, typically of 1 µM or less, preferably less than 500 nM or less than 100 nM or less than 50 nM, preferably as measured by the method described in Example 13—Measurements of "[$^3$H]-5-HT uptake into rat cortical synaptosomes".

Some compounds according to the invention inhibit the norepinephrine transporter and are thus norepinephrine reuptake inhibitors. The compounds typically have an in vitro uptake inhibition (IC50) of 5 µM or less, typically of 1 µM or less, preferably less than 500 nM, less than 100 nM or less than 50 nM, as measured by the method described in Example 13—Measurements of "[$^3$H]noradrenaline uptake into rat cortical synaptosomes".

Some compounds according to the invention inhibit the dopamine transporter and are thus dopamine reuptake inhibitors. Typically, such compounds have an in vitro uptake inhibition (IC50) of 5 µM or less, typically of 1 µM or less, preferably less than 500 nM, less than 100 nM or less than 50 nM, preferably as measured by the method described in Example 13—"Measurements of [$^3$H]dopamine uptake into rat cortical synaptosomes".

As already mentioned, the compounds according to the invention are serotonin reuptake inhibitors and they are thus considered to be applicable in the treatment of one or more of the following diseases/disorders: affective disorders, pain disorders, ADHD and stress urinary incontinence.

An embodiment concerns compounds of the invention having dual action, said compounds being serotonin reuptake inhibitors and norepinephrine reuptake inhibitors at the same time. Typically, such compounds have an in vitro uptake inhibition for the serotonin transporter which is at least 1, typically at least 5 or even more typically at least 10, 20 or 30 times higher than the in vitro uptake inhibition for the norepinephrine transporter as measured by the methods described in Example 13—"Measurements of [$^3$H]-5-HT uptake into rat cortical synaptosomes" and "Measurements of [$^3$H]noradrenaline uptake into rat cortical synaptosomes".

An embodiment concerns compounds of the invention having dual action, said compounds being serotonin reuptake inhibitors and dopamine reuptake inhibitors at the same time. Typically, such compounds have an in vitro uptake inhibition for the serotonin transporter which is at least 1, typically at least 5 or even more typically at least 10, 20 or 30 times higher than the in vitro uptake inhibition for the dopamine transporter as measured by the methods described in Example 13—"Measurements of [$^3$H]-5-HT uptake into rat cortical synaptosomes" and "Measurements of [$^3$H]dopamine uptake into rat cortical synaptosomes".

A further embodiment concerns compounds of the invention having triple action and thus being serotonin reuptake inhibitors, norepinephrine reuptake inhibitors and dopamine reuptake inhibitors.

In a further aspect the invention provides a compound of formula IV as the free base or a salt thereof for use as a medicament.

An embodiment of the invention provides a pharmaceutical composition comprising a compound of formula IV as the free base or a salt thereof and at least one pharmaceutically acceptable carrier or diluent. The composition may comprise any one of the embodiments of formula IV described above.

A further embodiment of the invention relates to the use of a compound of formula IV as the free base or a salt thereof for the preparation of a pharmaceutical composition for the treatment of a disease or disorder wherein a serotonin reuptake inhibitor is beneficial. Such pharmaceutical composition may comprise any one of the embodiments of formula IV described above.

A further embodiment of the invention relates to the use of a compound of formula IV as the free base or a salt thereof for the preparation of a pharmaceutical composition for the treatment of a disease or disorder, wherein a combined serotonin and norepinephrine reuptake inhibitor is beneficial. Such pharmaceutical composition may comprise any one of the embodiments of formula IV described above.

A further embodiment of the invention relates to the use of a compound of formula IV as the free base or a salt thereof for the preparation of a pharmaceutical composition for the treatment of a disease or disorder, wherein a combined serotonin and dopamine reuptake inhibitor is beneficial. Such pharmaceutical composition may comprise any one of the embodiments of formula IV described above.

A further embodiment of the present invention relates to the use of a compound of formula IV as the free base or a salt thereof for the preparation of a pharmaceutical composition for the treatment of a disease or disorder, wherein a combined serotonin, norepinephrine and dopamine reuptake inhibitor is beneficial. Such pharmaceutical composition may comprise any one of the embodiments of formula IV described above.

A further embodiment of the invention relates to the use of a compound of formula IV as the free base or a salt thereof for the preparation of a pharmaceutical composition for the treatment of affective disorders, pain disorders, ADHD and stress urinary incontinence.

In a further embodiment the present invention relates to the use of a compound of formula IV as the free base or a salt thereof for the preparation of a pharmaceutical composition for the treatment of affective disorders. To further illustrate without limiting the invention, the affective disorder to be treated is selected from the group consisting of depressive disorders and anxiety disorders.

A further embodiment concerns the use of a compound of formula IV as the free base or a salt thereof for the preparation of a pharmaceutical composition for the treatment of depressive disorders. Typically, the depressive disorder to be treated is selected from the group consisting of major depressive disorder, postnatal depression, dysthymia and depression associated with bipolar disorder, alzheimers, psychosis or parkinsons.

A further embodiment concerns the use of a compound of formula IV as the free base or a salt thereof for the preparation of a pharmaceutical composition for the treatment of anxiety disorders. Typically, the anxiety disorders to be treated are selected from the group consisting of general anxiety disorder, social anxiety disorder, post traumatic stress disorder, obsessive compulsive disorder, panic disorder, panic attacks, specific phobias, social phobia and agoraphobia.

In a further embodiment the present invention relates to the use of a compound of formula IV as the free base or a salt thereof for the preparation of a pharmaceutical composition for the treatment of pain disorders. To further illustrate without limiting the invention, the pain disorder to be treated is selected from the group consisting of fibromyalgia syndrome (FMS), overall pain, back pain, shoulder pain, headache as well as pain while awake and during daily activities.

In a further embodiment the present invention relates to the use of a compound of formula IV as the free base or a salt thereof for the preparation of a pharmaceutical composition for the treatment of attention deficit hyperactivity disorder.

In a further embodiment the present invention relates to the use of a compound of formula IV as the free base or a salt thereof for the preparation of a pharmaceutical composition for the treatment of stress urinary incontinence.

In a further aspect, the present invention relates to a method of preparing a compound of formula IV, comprising the nucleophilic substitution reaction of appropriately substituted indoles and appropriately substituted benzene sulfenyl chlorides.

The term "treatment" as used herein in connection with a disease or disorders includes also prevention as the case may be.

Pharmaceutical Compositions

The present invention also relates to a pharmaceutical composition. The compounds of the invention may be administered alone or in combination with pharmaceutically acceptable carriers or diluents, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

The compounds of this invention are generally utilized as the free substance or as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of a pharmaceutically acceptable acid. Representative examples are mentioned above.

Pharmaceutical compositions for oral administration may be solid or liquid. Solid dosage forms for oral administration include e.g. capsules, tablets, dragees, pills, lozenges, powders, granules and tablette e.g. placed in a hard gelatine capsule in powder or pellet form or e.g. in the form of a troche or lozenge. Where appropriate, pharmaceutical compositions for oral administration may be prepared with coatings such as enteric coatings or they can be formulated so as to provide controlled release of the active ingredient such as sustained or prolonged release according to methods well known in the art. Liquid dosage forms for oral administration include e.g. solutions, emulsions, suspensions, syrups and elixirs.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid, lower alkyl ethers of cellulose, corn starch, potato starch, gums and the like. Examples of liquid carriers are syrup, peanut oil, olive oil, phospho lipids, fatty acids, fatty acid amines, polyoxyethylene and water.

The carrier or diluent may include any sustained release material known in the art, such as glyceryl monostearate or glyceryl distearate, alone or mixed with a wax.

Any adjuvants or additives usually used for such purposes such as colourings, flavourings, preservatives etc. may be used provided that they are compatible with the active ingredients.

The amount of solid carrier may vary but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents and subsequently compressing the mixture in a conventional tabletting machine.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1, 2 or 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1, 2 or 3 times per day may contain from 0.01 to about 1000 mg, such as about 0.01 to 100 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

Typical examples of recipes for the formulation of the invention are as follows:

1) Tablets containing 5.0 mg of a compound of the invention calculated as the free base:

| | |
|---|---|
| Compound of the invention | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound of the invention | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| | |
|---|---|
| Compound of the invention | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per millilitre:

| | |
|---|---|
| Compound of the invention | 0.5 mg |
| Sorbitol | 5.1 mg |
| Acetic Acid | 0.05 mg |
| Saccharin sodium | 0.5 mg |
| Water | ad 1 mL |

By the expression a compound of the invention is meant any one of the embodiments of formula IV as described herein.

In a further aspect the present invention relates to a method of preparing a compound of the invention as described in the following.

Methods of Preparation of the Compounds of the Invention

General Methods

Compounds of formula IV may be prepared by conventional synthetic techniques as described in the methods below.

Method 1.

For the preparation of compounds of formula IV (for $R^1$, $R^2 \neq H$). The appropriate indole of formula V is combined with the appropriate sulfenyl chloride of formula VI (for $R^1$, $R^2 \neq H$) to generate the desired product of formula IV, using known methodology (Hamel P. et al. *J. Heterocyclic Chem.*, 1999, 36, 643). The product of formula IV is isolated as the free base or a salt thereof.

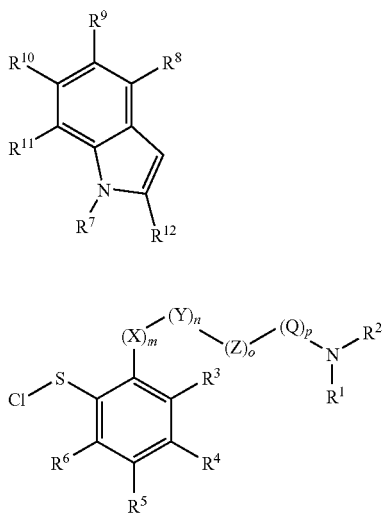

formula V

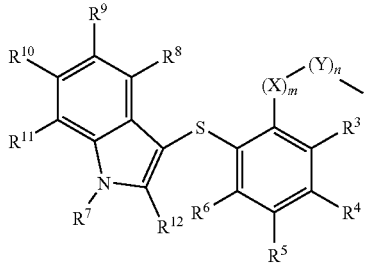

formula VI where $R^1$—$R^{12}$, X, Y, Z, Q, m, n, o, p are as defined herein.

Indoles of formula V are either commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known as suitable for such reactions.

Method 2.

For the preparation of compounds of formula IV with $R^1$=H. Compounds of formula VII are deprotected by standard techniques detailed in the textbook *Protective Groups in Organic Synthesis* Greene and Wuts, Wiley Interscience, (1999), ISBN 0471160199. The product of formula IV is isolated as the free base or a salt thereof.

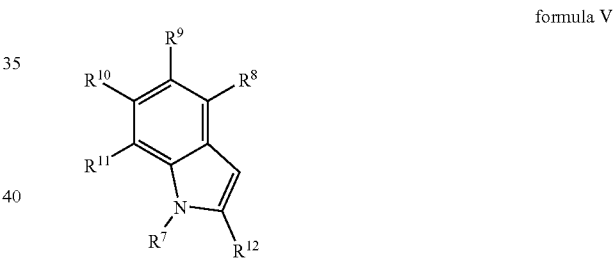

formula VII where $R^2$—$R^{12}$, X, Y, Z, Q, m, n, o, p are as defined herein and PG is a nitrogen protecting group.

Method 3.

For the preparation of compounds of formula IV (for $R^1$, $R^2 \neq H$). Compounds of formula VIII are treated with a reducing agent such as e.g. $LiAlH_4$ or $AlH_3$. The product of formula IV is isolated as the free base or a salt thereof.

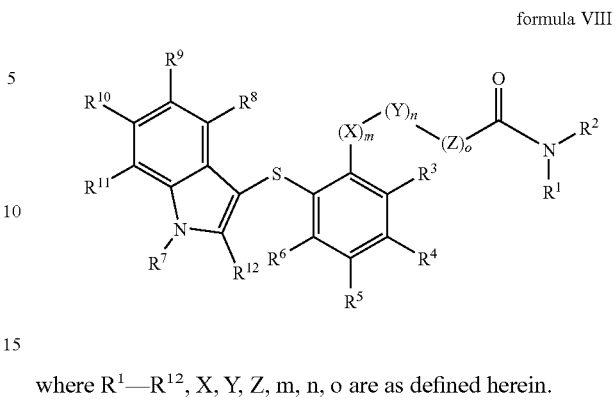

formula VIII where $R^1$—$R^{12}$, X, Y, Z, m, n, o are as defined herein.

Methods of Preparation of Intermediates for the Synthesis of Compounds of the Invention Intermediates for the synthesis of compounds of the invention may be prepared by conventional synthetic techniques as described in the methods below.

Method 4.

For the preparation of compounds of formula VII: The appropriate indole of formula V is combined with the appropriate sulfenyl chloride of formula IX using known methodology (Hamel P. et al. *J. Heterocyclic Chem.*, 1999, 36, 643).

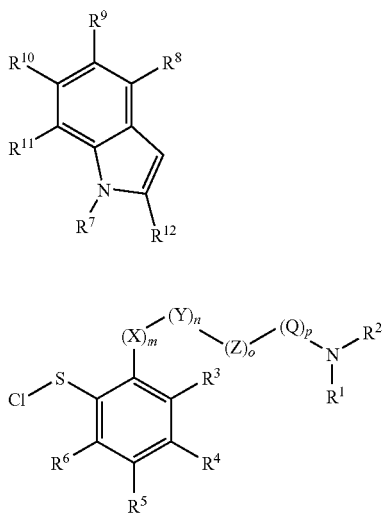

formula V

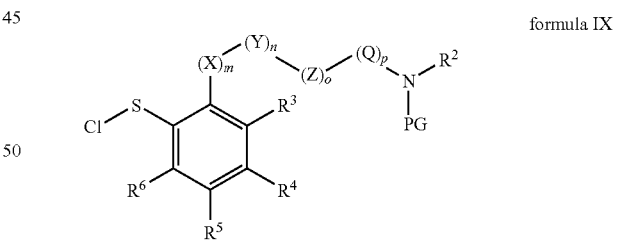

formula IX where $R^2$—$R^{12}$, X, Y, Z, Q, m, n, o, p are as defined herein and PG is a nitrogen protecting group.

Method 5.

For the preparation of compounds of formula VI (for $R^1$, $R^2 \neq H$) and for the preparation of compounds of formula IX: Reaction of a thiophenol of formula X (for $R^1$, $R^2 \neq H$) or of a thiophenol of formula XI with a chlorinating reagent such as N-chloro succinimide.

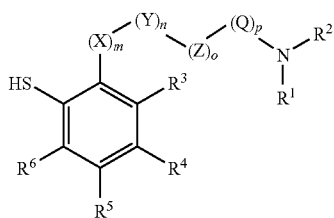

formula X

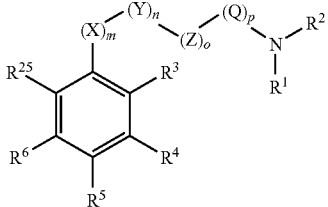

formula XIV

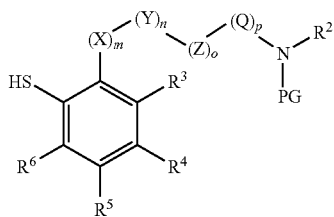

formula XI

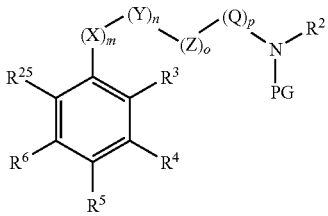

formula XV

HS—SPG formula XVI where $R^1$—$R^6$, X, Y, Z, Q, m, n, o, p are as defined herein and PG is a nitrogen protecting group.

Method 6.

For the preparation of compounds of formula X (for $R^1$, $R^2 \neq H$) and of compounds of formula XI: Deprotection of the thiol moiety of a protected thiol of formula XII (for $R^1$, $R^2 \neq H$) or of a protected thiol of formula XIII, by e.g. using a fluoride donor such as e.g. triethylamine tris(hydrogen fluoride).

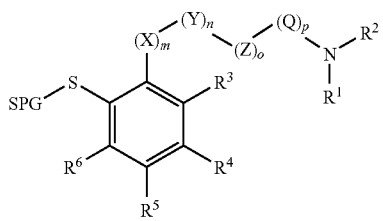

formula XII

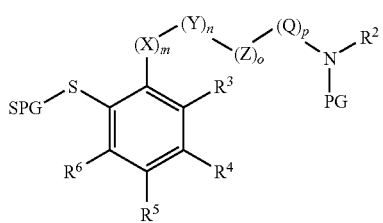

formula XIII where $R^1$—$R^{12}$, X, Y, Z, Q, m, n, o, p are as defined herein, PG is a nitrogen protecting group and SPG is a thiol protecting group, e.g. a tri-iso-propyl silyl group.

Method 7.

For the preparation of compounds of formula XII (for $R^1$, $R^2 \neq H$) and compounds of formula XIII: Reaction of a compound of formula XIV (for $R^1$, $R^2 \neq H$) or of a compound of formula XV with a protected thiol of formula XVI in the presence of a palladium catalyst and an appropriate base, according to Arnould, J. C. et al. *Tetrahedron Letters*, 1996, 37, 4523 and Winn M. et al. *J. Med. Chem.*, 2001, 44, 4393.

where $R^1$—$R^{12}$, X, Y, Z, Q, m, n, o, p are as defined herein, PG is a nitrogen protecting group, SPG is a thiol protecting group, e.g. a tri-iso-propyl silyl group and $R^{25}$ is a halogen such as iodine or bromine or $R^{25}$ is a pseudo halogen such as e.g. a trifluoro methyl sulphonyl group or a nonafluoro butyl sulphonyl group.

Method 8.

For the preparation of compounds of formula XIV (for $R^1$, $R^2 \neq H$; Q=CH$_2$) and for the preparation of compounds of formula XV (for Q=CH$_2$): Reduction of an amide of formula XVII (for $R^1$, $R^2 \neq H$) or reduction of an amide of formula XVIII followed by protection of the nitrogen moiety with a nitrogen protecting group.

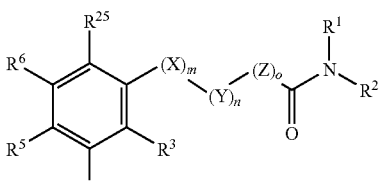

formula XVII

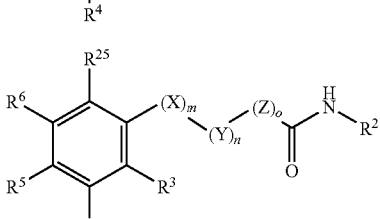

formula XVIII where $R^1$—$R^6$, X, Y, Z, m, n, o are as defined herein and $R^{25}$ is a halogen such as iodine or bromine or $R^{25}$ is a pseudo halogen such as e.g. a trifluoro methyl sulphonyl group or a nonafluoro butyl sulphonyl group.

Method 9.

For the preparation of compounds of formula XVII and for the preparation of compounds of formula XVIII: Activation of a carboxylic acid of formula XIX with an activating reagent such as e.g. thionyl chloride, N,N'-dicyclohexylcarbodiimide or carbonyl diimidazole followed by reaction with an amine of formula XX.

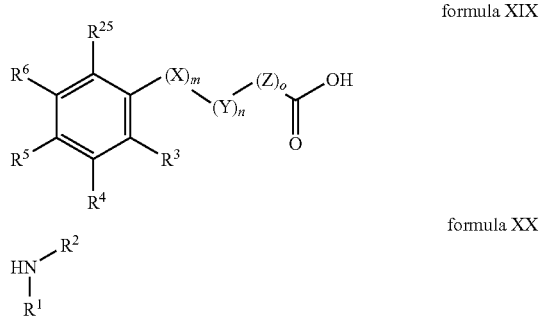

formula XIX formula XX where $R^1$—$R^6$, X, Y, Z, m, n, o are as defined herein and $R^{25}$ is a halogen such as iodine or bromine or $R^{25}$ is a pseudo halogen such as e.g. a trifluoro methyl sulphonyl group or a nonafluoro butyl sulphonyl group. Amines of formula XX are commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known as suitable for such reactions.

Method 10.

For the preparation of compounds of formula XIV (for $R^1$, $R^2 \neq H$; $Q=CH_2$ or $CHR^{22}$) and for the preparation of compounds of formula XV (for $Q=CH_2$ or $CHR^{22}$): Reductive amination of an aldehyde of formula XXI or of a ketone of formula XXII with an amine of formula XX, using a reducing reagent such as e.g. sodium cyanoborohydride. For $R^1=H$, the reductive amination is followed by protection of nitrogen moiety with a nitrogen protecting group.

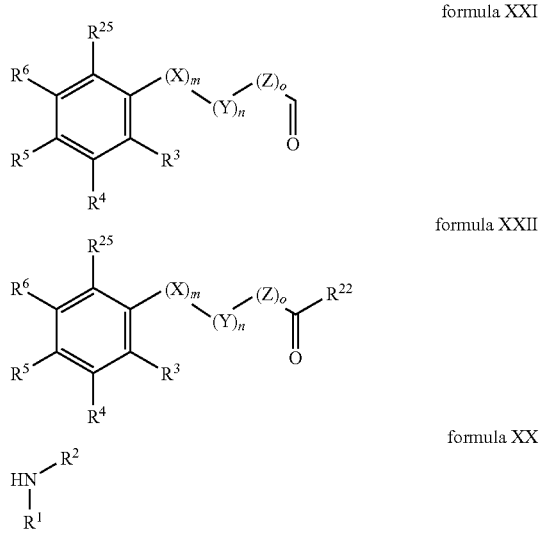

formula XXI formula XXII formula XX where $R^1$—$R^6$, $R^{22}$ X, Y, Z, m, n, o are as defined herein and $R^{25}$ is a halogen such as iodine or bromine or $R^{25}$ is a pseudo halogen such as e.g. a trifluoro methyl sulphonyl group or a nonafluoro butyl sulphonyl group.

Method 11.

For the preparation of compounds of formula XXI (for n=1, $X=CH_2$, $Y=CH_2$, $CHR^{16}$) and for the preparation of compounds of formula XXII (for n=1, $X=CH_2$, $Y=CH_2$, $CHR^{16}$): A tandem Heck—isomerization reaction of a 1-bromo-2-iodobenzene compound of formula XXIII and an olefin of formula XXIV or of formula XXV according to Gibson et al. Synlett 1999, 954 and Qadir et al. Tetrahedron Letters, 44, 2003, 3675.

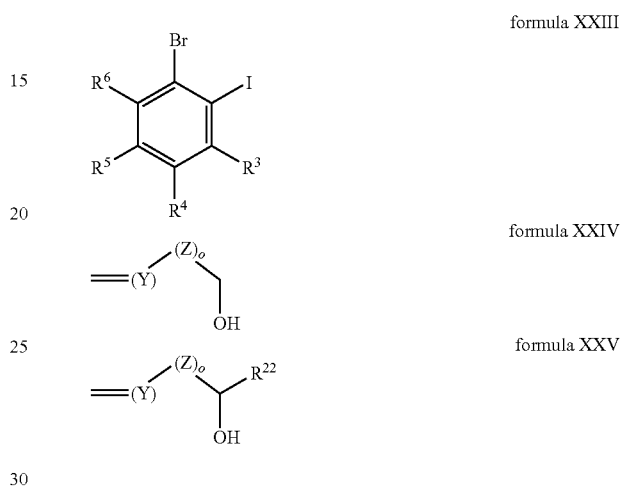

formula XXIII formula XXIV formula XXV where $R^1$—$R^6$, $R^{22}$, Y, Z, o are as defined herein. 1-Bromo-2-iodobenzene compounds of formula XXIII, olefins of formula XXIV or of formula XXV are commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known as suitable for such reactions.

Method 12.

For the preparation of compounds of formula VIII: Activation of a carboxylic acid of formula XXVI with an activating reagent such as e.g. carbonyl diimidazole followed by reaction with an amine of formula XX.

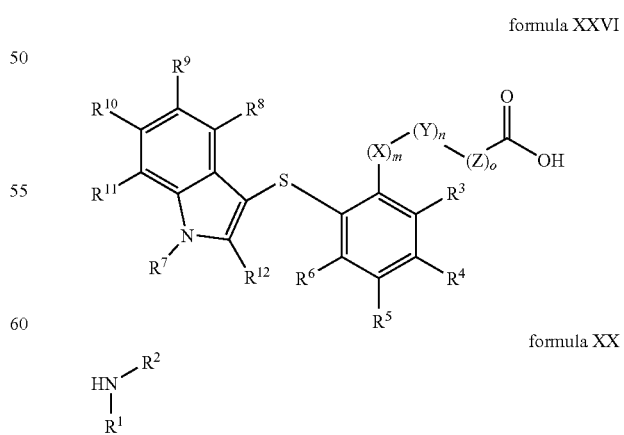

formula XXVI formula XX where $R^1$—$R^{12}$, X, Y, Z, m, n, o are as defined herein.

Method 13.

For the preparation of compounds of formula XXVI: Hydrolysis of a carboxylic acid ester of formula XXVII.

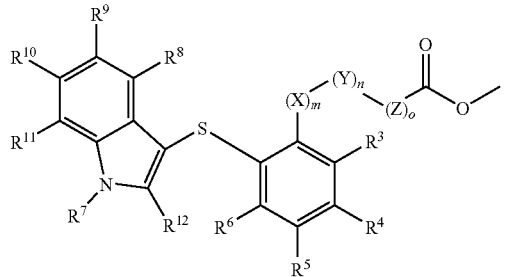

formula XXVII where $R^3$—$R^{12}$, X, Y, Z, m, n, o are as defined herein.

Method 14.

For the preparation of compounds of formula XXVII: The appropriate indole of formula V is combined with the appropriate sulfenyl chloride of formula XXVIII to generate desired product of formula XXVII, using known methodology (Hamel P. et al. *J. Heterocyclic Chem.*, 1999, 36, 643).

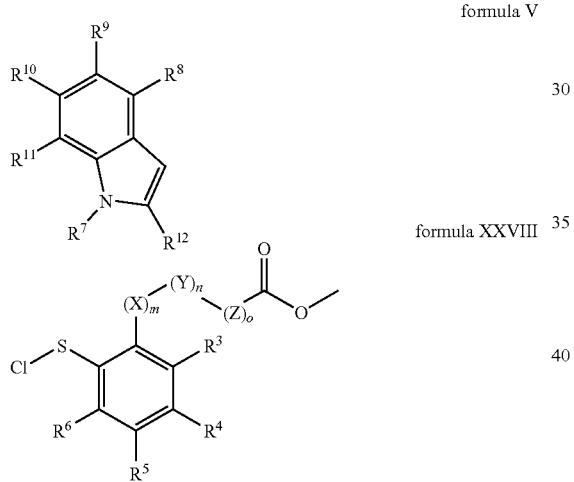

formula V formula XXVIII where $R^3$—$R^{12}$, X, Y, Z, m, n, o are as defined herein.

Method 15.

For the preparation of compounds of formula XXVIII: Reaction of a thiophenol of formula XXIX with a chlorinating reagent such as N-chloro succinimide.

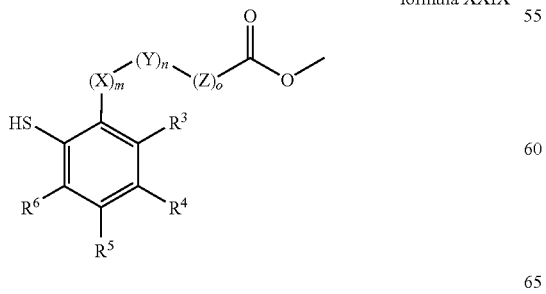

formula XXIX where $R^3$—$R^6$, X, Y, Z, m, n, o are as defined herein.

Method 16.

For the preparation of compounds of formula XXIX: Deprotection of the thiol moiety of a protected thiol of formula XXX.

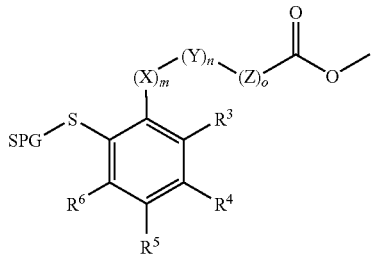

formula XXX where $R^3$—$R^6$, X, Y, Z, m, n, o are as defined herein and SPG is a thiol protecting group, e.g. a tri-iso-propyl silyl group or a methoxycarbonyl ethyl group.

Method 17.

For the preparation of compounds of formula XXX: Reaction of a compound of formula XXXI with a protected thiol of formula XVI in the presence of a palladium catalyst and an appropriate base according to Arnould, J. C. et al. *Tetrahedron Letters*, 1996, 37, 4523 and Winn M. et al. *J. Med. Chem.*, 2001, 44, 4393.

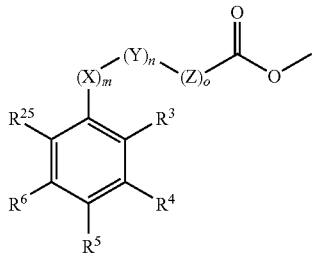

formula XXXI

HS—SPG    formula XVI where $R^3$—$R^6$, X, Y, Z, m, n, o are as defined herein, SPG is a thiol protecting group, e.g. a tri-iso-propyl silyl group or a methoxycarbonyl ethyl group, and $R^{25}$ is a halogen such as iodine or bromine or $R^{25}$ is a pseudo halogen such as e.g. a trifluoro methyl sulphonyl group or a nonafluoro butyl sulphonyl group.

Method 18.

For the preparation of compounds of formula XXXI: Fischer esterification of a carboxylic acid of formula XXXII:

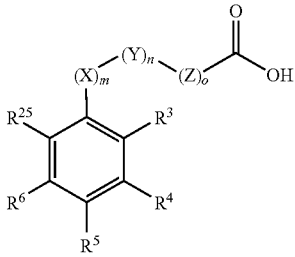

formula XXXII where $R^3$—$R^6$, X, Y, Z, m, n, o are as defined herein, and $R^{25}$ is a halogen such as iodine or bromine. Carboxylic acids of formula XXXII are commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known as suitable for such reactions.

EXAMPLES

Analytical LC-MS data (Method A) were obtained on a PE Sciex API 150EX instrument equipped with atmospheric pressure photo ionisation and a Shimadzu LC-8A/SLC-10A LC system. Column: 30×4.6 mm Waters Symmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A/10% B to 100% B in 4 minutes and with a flow rate of 2 mL/minute. Purity was determined by integration of the UV (254 nm) and ELSD trace. The retention times ($t_R$) are expressed in minutes.

Preparative LC-MS-purification was performed on the same instrument with atmospheric pressure chemical ionisation. Column: 50×20 mm YMC ODS-A with 5 μm particle size; Method: Linear gradient elution with 80% A to 100% B in 7 minutes and with a flow rate of 22.7 mL/minute. Fraction collection was performed by split-flow MS detection.

Analytical LC-MS-TOF (TOF=time of flight) data (Method B) were obtained on a micromass LCT 4-ways MUX equipped with a Waters 2488/Sedex 754 detector system. Column: 30×4.6 mm Waters Symmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A/10% B to 100% B in 4 minutes and with a flow rate of 2 mL/minute. Purity was determined by integration of the UV (254 nm) and ELSD trace. The retention times ($t_R$) are expressed in minutes.

The invention disclosed herein is further illustrated by the following non-limiting examples.

Preparation of the Compounds of the Invention

Example 1

Synthesis of 1. {2-[5-fluoro-2-(1H-indol-3-ylsulfanyl)-phenyl]-ethyl}-methyl-amine (Method 2)

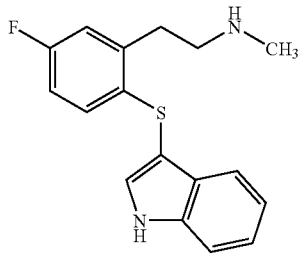

{2-[5-Fluoro-2-(1H-indol-3-ylsulfanyl)-phenyl]-ethyl}-methyl-carbamic acid tert-butyl ester (99 mg, 0.24 mmol) is dissolved in methanol (1.5 mL) and diethyl ether saturated with hydrochloric acid (0.5 mL) is added. The mixture is stirred at ambient temperature for 2 hours and concentrated in vacuo. Water (5 mL) is added to the remanence and the mixture is basified by addition of aqueous ammonia (25%). The aqueous fraction is extracted with ethyl acetate (3×10 mL). The combined organic fractions are dried ($MgSO_4$) and concentrated in vacuo. The product is purified by preparative HPLC or silica gel chromatography eluting with ethyl acetate-ethanol-triethyl amine (100:5:5) to give 62 mg (83%) of the title compound.

The following compounds were prepared analogously:

2. {2-[2-(6-Fluoro-1H-indol-3-ylsulfanyl)-phenyl]-ethyl}-methyl-amine

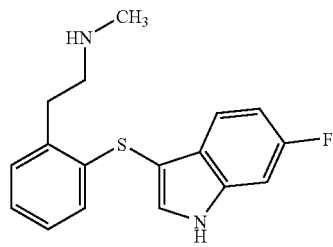

3. {2-[2-(5-Fluoro-1H-indol-3-ylsulfanyl)-phenyl]-ethyl}-methyl-amine

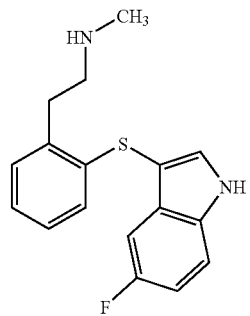

4. {2-[2-(4-Fluoro-1H-indol-3-ylsulfanyl)-phenyl]-ethyl}-methyl-amine

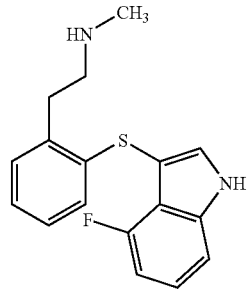

5. {2-[2-(7-Fluoro-1H-indol-3-ylsulfanyl)-phenyl]-ethyl}-methyl-amine

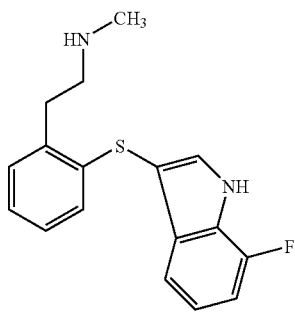

6. {2-[2-(7-Methoxy-1H-indol-3-ylsulfanyl)-phenyl]-ethyl}-methyl-amine

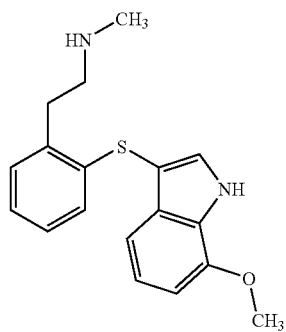

7. {2-[2-(5-Fluoro-2-methyl-1H-indol-3-ylsulfanyl)-phenyl]-ethyl}-methyl-amine

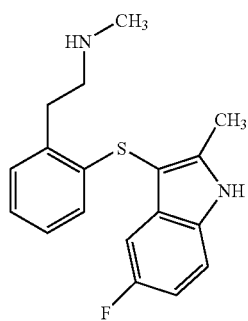

8. {2-[2-(5-Chloro-1H-indol-3-ylsulfanyl)-phenyl]-ethyl}-methyl-amine

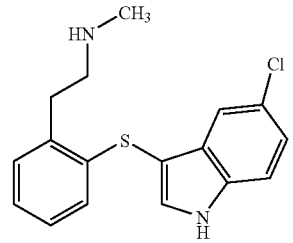

9. {2-[2-(4-Chloro-1H-indol-3-ylsulfanyl)-phenyl]-ethyl}-methyl-amine

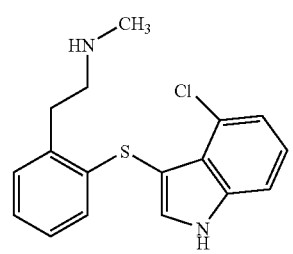

10. {2-[2-(7-Chloro-1H-indol-3-ylsulfanyl)-phenyl]-ethyl}-methyl-amine

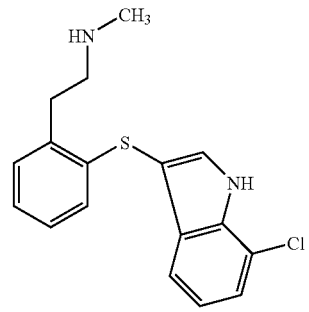

11. {2-[2-(1H-Indol-3-ylsulfanyl)-phenyl]-ethyl}-methyl-amine

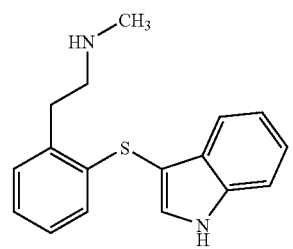

12. {2-[2-(1-Methyl-indol-3-ylsulfanyl)-phenyl]-ethyl}-methyl-amine
15. {2-[5-Chloro-2-(4-chloro-1H-indol-3-ylsulfanyl)-phenyl]-ethyl}-methyl-amine
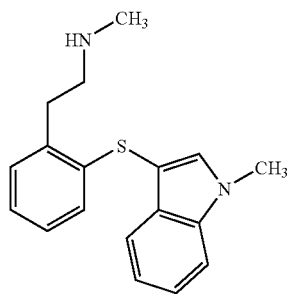
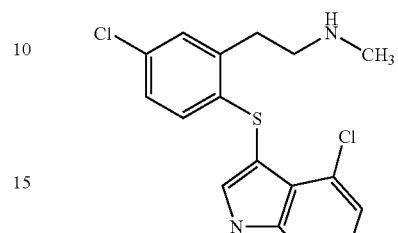
13. {2-[5-Chloro-2-(1H-indol-3-ylsulfanyl)-phenyl]-ethyl}-methyl-amine
16. {2-[5-Fluoro-2-(6-fluoro-1H-indol-3-ylsulfanyl)-phenyl]-ethyl}-methyl-amine
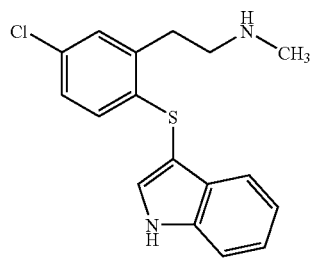
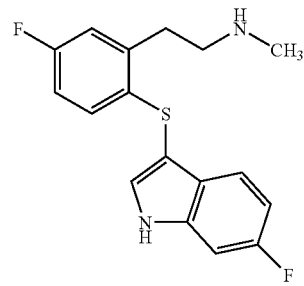
14. {2-[5-Chloro-2-(6-fluoro-1H-indol-3-ylsulfanyl)-phenyl]-ethyl}-methyl-amine
17. (2-(2-(4-Chloro-1H-indol-3-ylsulfanyl)-5-fluoro-phenyl)-ethyl)-methyl-amine
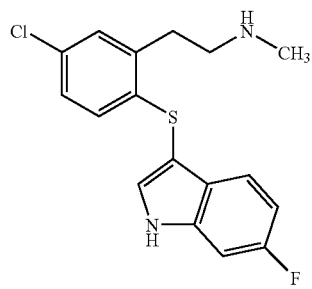
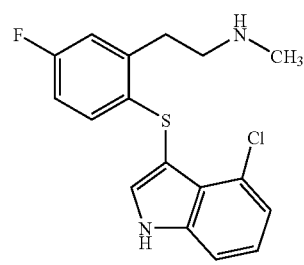

18. {2-[2-(6-Fluoro-1H-indol-3-ylsulfanyl)-4,5-dimethoxy-phenyl]-ethyl}-methyl-amine

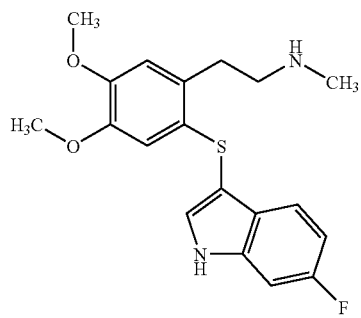

19. {2-[2-(4-Chloro-1H-indol-3-ylsulfanyl)-4,5-dimethoxy-phenyl]-ethyl}-methyl-amine

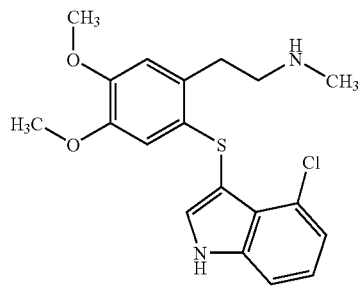

20. {2-[2-(1H-Indol-3-ylsulfanyl)-4,5-dimethoxy-phenyl]-ethyl}-methyl-amine

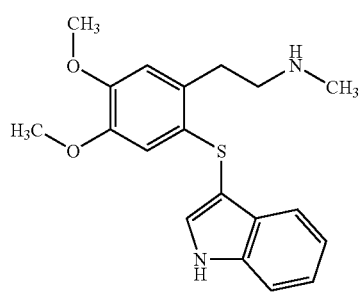

21. {4-[2-(1H-Indol-3-ylsulfanyl)-phenyl]-butyl}-methyl-amine

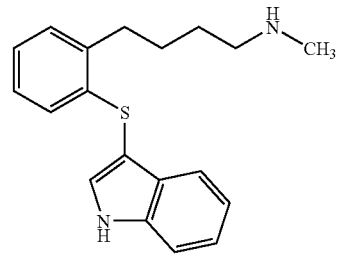

22. {4-[2-(4-Methoxy-1H-indol-3-ylsulfanyl)-phenyl]-butyl}-methyl-amine

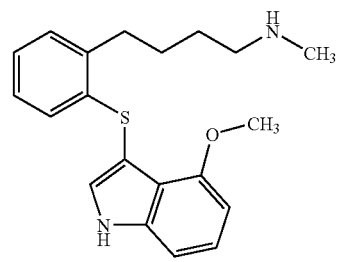

23. {4-[2-(4-Chloro-1H-indol-3-ylsulfanyl)-phenyl]-butyl}-methyl-amine

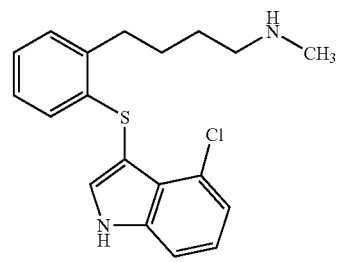

24. Methyl-{4-[2-(1-methyl-1H-indol-3-ylsulfanyl)-phenyl]-butyl}-amine

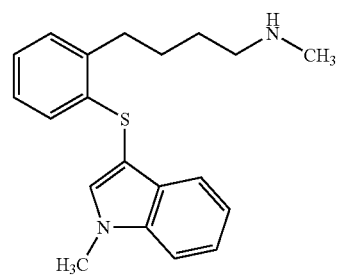

The following compounds were prepared analogously:

25. {3-[2-(4-Chloro-1H-indol-3-ylsulfanyl)-phenyl]-propyl}-methyl-amine

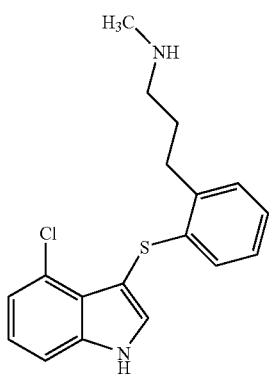

26. {3-[2-(4-Methoxy-1H-indol-3-ylsulfanyl)-phenyl]-propyl}-methyl-amine

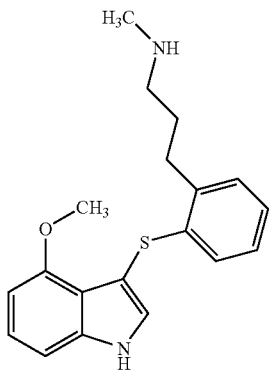

The following compound is prepared analogously:

27. Dimethyl-{3-[2-(3-methylamino-propyl)-phenylsulfanyl]-1H-indol-5-yl}-amine

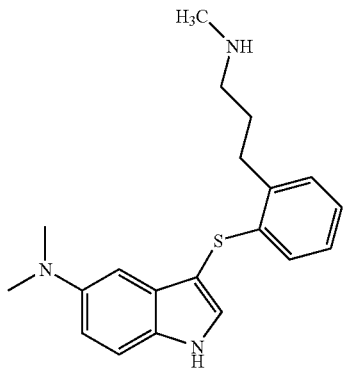

28. Methyl-{3-[2-(7-nitro-1H-indol-3-ylsulfanyl)-phenyl]-propyl}-amine

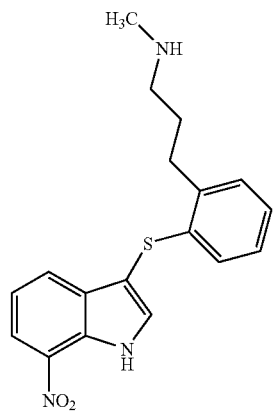

The following compounds were prepared analogously:

29. {3-[2-(6-Methanesulfonyl-1H-indol-3-ylsulfanyl)-phenyl]-propyl}-methyl-amine

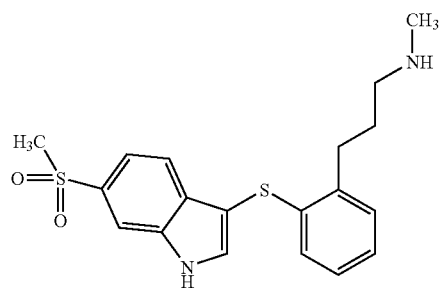

30. {3-[2-(1H-Indol-3-ylsulfanyl)-phenyl]-propyl}-methyl-amine

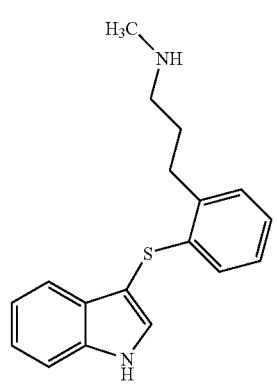

31. {3-[2-(6-Fluoro-1H-indol-3-ylsulfanyl)-phenyl]-propyl}-methyl-amine

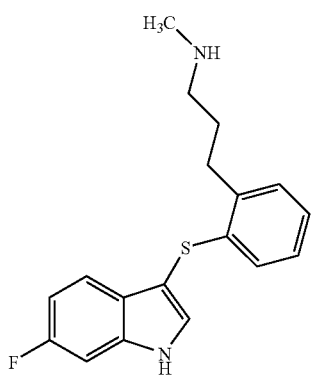

The following compound is prepared analogously:

32. Methyl-{3-[2-(1-methyl-1H-indol-3-ylsulfanyl)-phenyl]-propyl}-amine

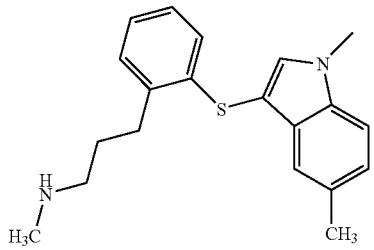

The following compound was prepared analogously:

33. Methyl-{3-[2-(5-methyl-1H-indol-3-ylsulfanyl)-phenyl]-propyl}-amine

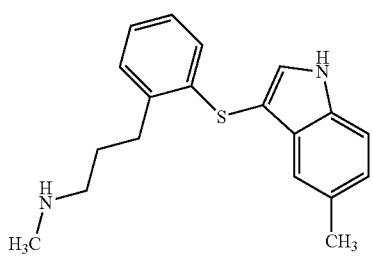

Analytical data of compounds 1-24 are shown in Table 2.

Example 2

Synthesis of 35. {2-[2-(1H-indol-3-ylsulfanyl)-phenyl]-ethyl}-dimethyl-amine (Method 3.)

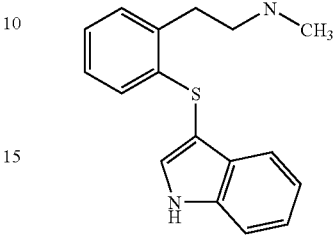

2-[2-(1H-Indol-3-ylsulfanyl)-phenyl]-N,N-dimethyl-acetamide (116 mg, 0.37 mmol) in 6 mL THF is added to LiAlH$_4$ (43 mg, 1.12 mmol) in 4 mL THF. The reaction mixture is stirred 16 hours at 50° C. The reaction is quenched with water and 2N NaOH. The reaction mixture is stirred for 1 hour, then 2.5 mL water is added and stirring was continued for another hour. The mixture is filtered, dried with MgSO$_4$ and concentrated in vacuo. Purification by flash chromatography or preparative HPLC to gives the title compound. The following compounds were prepared analogously:

36. 3-[2-(2-Morpholin-4-yl-ethyl)-phenylsulfanyl]-1H-indole

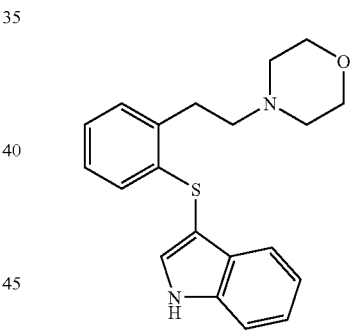

37. 3-[2-(2-Thiomorpholin-4-yl-ethyl)-phenylsulfanyl]-1H-indole

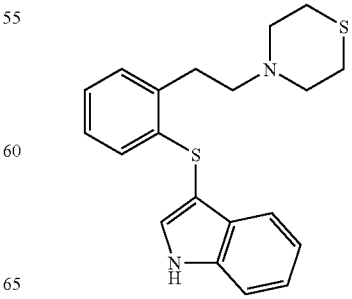

The following compound is prepared analogously:

34. 2-[2-(1H-Indol-3-ylsulfanyl)-phenyl]-ethylamine

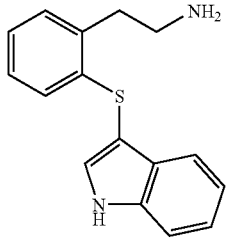

Preparation of Intermediates

Example 3

Synthesis of {2-[5-Fluoro-2-(1H-indol-3-ylsulfanyl)-phenyl]-ethyl}-methyl-carbamic acid tert-butyl ester (Method 4, Method 5, Method 14, Method 15.)

[2-(5-Fluoro-2-mercapto-phenyl)-ethyl]-methyl-carbamic acid tert-butyl ester (240 mg, 0.84 mmol) is dissolved in dry THF (3 mL) and added dropwise to a solution of N-chlorosuccinimide (112 mg, 0.84 mmol) in 1,2-dichloroethane (3 mL) at 0° C. The mixture is allowed to heat to ambient temperature and is stirred for 30 minutes. The resulting sulfenyl chloride solution is added dropwise to a solution of 1H-indole (147 mg, 1.26 mmol) in dry THF (3 mL) at 0° C. The mixture is stirred for 15 minutes at 0° C. before adding saturated sodium bicarbonate solution (15 mL). The mixture is extracted with ethyl acetate (3×20 mL) and the combined organic fractions are washed with brine, dried (MgSO$_4$) and concentrated in vacuo. The product is purified by silica gel chromatography eluting with ethyl acetate-heptane, first (1:10) then (1:4). Upon evaporation of the volatiles 99 mg (29%) of the title compound is isolated.

The following intermediates were prepared analogously:
{2-[5-Fluoro-2-(1H-indol-3-ylsulfanyl)-phenyl]-ethyl}-methyl-carbamic acid tert-butyl ester
{2-[2-(6-Fluoro-1H-indol-3-ylsulfanyl)-phenyl]-ethyl}-methyl-carbamic acid tert-butyl ester
{2-[2-(5-Fluoro-1H-indol-3-ylsulfanyl)-phenyl]-ethyl}-methyl-carbamic acid tert-butyl ester
{2-[2-(4-Fluoro-1H-indol-3-ylsulfanyl)-phenyl]-ethyl}-methyl-carbamic acid tert-butyl ester
{2-[2-(7-Fluoro-1H-indol-3-ylsulfanyl)-phenyl]-ethyl}-methyl-carbamic acid tert-butyl ester
{2-[2-(7-Methoxy-1H-indol-3-ylsulfanyl)-phenyl]-ethyl}-methyl-carbamic acid tert-butyl ester
{2-[2-(5-Fluoro-2-methyl-1H-indol-3-ylsulfanyl)-phenyl]-ethyl}-methyl-carbamic acid tert-butyl ester
{2-[2-(5-Chloro-1H-indol-3-ylsulfanyl)-phenyl]-ethyl}-methyl-carbamic acid tert-butyl ester
{2-[2-(4-Chloro-1H-indol-3-ylsulfanyl)-phenyl]-ethyl}-methyl-carbamic acid tert-butyl ester
{2-[2-(7-Chloro-1H-indol-3-ylsulfanyl)-phenyl]-ethyl}-methyl-carbamic acid tert-butyl ester
{2-[2-(1H-Indol-3-ylsulfanyl)-phenyl]-ethyl}-methyl-carbamic acid tert-butyl ester
{2-[2-(1-Methyl-indol-3-ylsulfanyl)-phenyl]-ethyl}-methyl-carbamic acid tert-butyl ester
{2-[5-Chloro-2-(1H-indol-3-ylsulfanyl)-phenyl]-ethyl}-methyl-carbamic acid tert-butyl ester
{2-[5-Chloro-2-(6-fluoro-1H-indol-3-ylsulfanyl)-phenyl]-ethyl}-methyl-carbamic acid tert-butyl ester
{2-[5-Chloro-2-(4-chloro-1H-indol-3-ylsulfanyl)-phenyl]-ethyl}-methyl-carbamic acid tert-butyl ester
{2-[5-Fluoro-2-(6-fluoro-1H-indol-3-ylsulfanyl)-phenyl]-ethyl}-methyl-carbamic acid tert-butyl ester
(2-(2-(4-Chloro-1H-indol-3-ylsulfanyl)-5-fluoro-phenyl)-ethyl)-methyl-carbamic acid tert-butyl ester
{2-[2-(6-Fluoro-1H-indol-3-ylsulfanyl)-4,5-dimethoxy-phenyl]-ethyl}-methyl-carbamic acid tert-butyl ester
{2-[2-(4-Chloro-1H-indol-3-ylsulfanyl)-4,5-dimethoxy-phenyl]-ethyl}-methyl-carbamic acid tert-butyl ester
{2-[2-(1H-Indol-3-ylsulfanyl)-4,5-dimethoxy-phenyl]-ethyl}-methyl-carbamic acid tert-butyl ester
{4-[2-(1H-Indol-3-ylsulfanyl)-phenyl]-butyl}-methyl-carbamic acid tert-butyl ester
4-[2-(4-Methoxy-1H-indol-3-ylsulfanyl)-phenyl]-butylcarbamic acid tert-butyl ester
{4-[2-(4-Chloro-1H-indol-3-ylsulfanyl)-phenyl]-butyl}-methyl-carbamic acid tert-butyl ester
Methyl-{4-[2-(1-methyl-1H-indol-3-ylsulfanyl)-phenyl]-butyl}-carbamic acid tert-butyl ester
[2-(1H-Indol-3-ylsulfanyl)-phenyl]-acetic acid methyl ester The following intermediates are prepared analogously:
{3-[2-(4-Chloro-1H-indol-3-ylsulfanyl)-phenyl]-propyl}-methyl-carbamic acid tert-butyl ester
{3-[2-(4-Methoxy-1H-indol-3-ylsulfanyl)-phenyl]-propyl}-methyl-carbamic acid tert-butyl ester
{3-[2-(5-Dimethylamino-1H-indol-3-ylsulfanyl)-phenyl]-propyl}-methyl-carbamic acid tert-butyl ester
Methyl-{3-[2-(7-nitro-1H-indol-3-ylsulfanyl)-phenyl]-propyl}-carbamic acid tert-butyl ester
{3-[2-(6-Methanesulfonyl-1H-indol-3-ylsulfanyl)-phenyl]-propyl}-methyl-carbamic acid tert-butyl ester
{3-[2-(1H-Indol-3-ylsulfanyl)-phenyl]-propyl}-methyl-carbamic acid tert-butyl ester
{3-[2-(6-Fluoro-1H-indol-3-ylsulfanyl)-phenyl]-propyl}-methyl-carbamic acid tert-butyl ester
Methyl-{3-[2-(1-methyl-1H-indol-3-ylsulfanyl)-phenyl]-propyl}-carbamic acid tert-butyl ester
Methyl-{3-[2-(5-methyl-1H-indol-3-ylsulfanyl)-phenyl]-propyl}-carbamic acid tert-butyl ester Example 4

Synthesis of [2-(5-fluoro-2-mercapto-phenyl)-ethyl]-methyl-carbamic acid tert-butyl ester (Method 6, Method 16.)

[2-(5-Fluoro-2-triisopropylsilanylsulfanyl-phenyl)-ethyl]-methyl-carbamic acid tert-butyl ester (1.60 g, 3.62 mmol) is dissolved in dry THF (12 mL) and triethylamine trihydrofluoride (0.59 g, 3.66 mmol) is added. The resulting mixture is heated at 60° C. for 5 minutes, then cooled and concentrated in vacuo. The product is purified by eluting through a plug of silica with ethyl acetate-heptane (1:4) to give 0.72 g (72%) of the title compound as an oil.

The following intermediates were prepared analogously:
[2-(2-Mercapto-phenyl)-ethyl]-methyl-carbamic acid tert-butyl ester
[2-(5-Chloro-2-mercapto-phenyl)-ethyl]-methyl-carbamic acid tert-butyl ester
[2-(2-Mercapto-4,5-dimethoxy-phenyl)-ethyl]-methyl-carbamic acid tert-butyl ester

[4-(2-Mercapto-phenyl)-butyl]-methyl-carbamic acid tert-butyl ester
(2-Mercapto-phenyl)-acetic acid methyl ester
[3-(2-Mercapto-phenyl)-propyl]-methyl-carbamic acid tert-butyl ester

Example 5

Synthesis of [2-(5-fluoro-2-triisopropylsilanylsulfanyl-phenyl)-ethyl]-methyl-carbamic acid tert-butyl ester (Method 7, Method 17.)

[2-(2-Bromo-5-fluoro-phenyl)-ethyl]-methyl-carbamic acid tert-butyl ester (3.0 g, 9.03 mmol), tris(dibenzylideneacetone)dipalladium (0) (83 mg, 0.09 mmol), bis(2-diphenylphosphinophenyl)ether (97 mg, 0.18 mmol), sodium tert-butoxide (1.10 g, 11.7 mmol), triisopropylsilanethiol (1.90 g, 9.93 mmol) and dry toluene (15 mL) are all placed in an Emrys Optimizer EXP 20 mL microwave reactor tube. The reaction vessel is sealed and subjected to microwave heating at 160° C. for 15 minutes. Upon cooling the mixture is poured onto a plug of silica and the product is eluted with ethyl acetate-heptane (1:10). This furnishes 1.6 g (40%) of the title compound as an oil, which is used in the next step without further purification.

The following intermediates were prepared analogously:
Methyl-[2-(2-triisopropylsilanylsulfanyl-phenyl)-ethyl]-carbamic acid tert-butyl ester
[2-(5-Chloro-2-triisopropylsilanylsulfanyl-phenyl)-ethyl]-methyl-carbamic acid tert-butyl ester
[2-(4,5-Dimethoxy-2-triisopropylsilanylsulfanyl-phenyl)-ethyl]-methyl-carbamic acid tert-butyl ester
Methyl-[4-(2-triisopropylsilanylsulfanyl-phenyl)-butyl]-carbamic acid tert-butyl ester
(2-Triisopropylsilanylsulfanyl-phenyl)-acetic acid methyl ester
Methyl-[3-(2-triisopropylsilanylsulfanyl-phenyl)-propyl]-carbamic acid tert-butyl ester

Example 6

Synthesis of [2-(2-bromo-5-fluoro-phenyl)-ethyl]-methyl-amine (Method 8)

Lithium aluminum hydride (7.50 g, 197 mmol) is suspended in dry diethyl ether (75 mL) and cooled to 0° C. Aluminum (III) chloride (8.80 g, 65.8 mmol) dissolved in dry diethyl ether (75 mL) is added dropwise at 0-5° C. The cooling bath is removed and the mixture is stirred at ambient temperature for 1 hour. The resulting aluminum hydride reagent solution is cooled to 0° C. followed by dropwise addition of 2-(2-bromo-5-fluoro-phenyl)-N-methyl-acetamide (16.2 g, 65.8 mmol) dissolved in dry THF (150 mL). After complete addition the solution is allowed to heat to ambient temperature and stirring is continued for 16 hours. The mixture is cooled to 10° C. followed by slow dropwise addition of water (16 mL) followed by 2M sodium hydroxide (16 mL) and water (80 mL) to quench excessive reducing agent. The mixture is filtered and concentrated in vacuo. The remanence is redissolved in ethyl acetate (200 mL), dried (MgSO$_4$) and concentrated again to give 14.6 g (95%) of the title compound as an oil.

The following intermediates were prepared analogously:
[2-(2-Iodo-phenyl)-ethyl]-methyl-amine
[2-(2-Bromo-5-chloro-phenyl)-ethyl]-methyl-amine
[2-(2-Bromo-4,5-dimethoxy-phenyl)-ethyl]-methyl-amine
[4-(2-Bromo-phenyl)-butyl]-methyl-amine Synthesis of [2-(2-bromo-5-fluoro-phenyl)-ethyl]-methyl-carbamic acid tert-butyl ester (Method 8)

[2-(2-Bromo-5-fluoro-phenyl)-ethyl]-methyl-amine (14.6 g, 62.9 mmol) is dissolved in dry THF (200 mL) and di-tert-butyl dicarbonate (15.1 g, 69.2 mmol) is added. The mixture is stirred for 16 hours at ambient temperature. The volatiles are removed by means of evaporation and the crude mixture is purified by silica gel chromatography eluting with ethyl acetate-heptane (1:4) to furnish 19.4 g (93%) of the title compound as an oil.

The following intermediates were prepared analogously:
[2-(2-Iodo-phenyl)-ethyl]-methyl-carbamic acid tert-butyl ester
[2-(2-Bromo-5-chloro-phenyl)-ethyl]-methyl-carbamic acid tert-butyl ester
[2-(2-Bromo-4,5-dimethoxy-phenyl)-ethyl]-methyl-carbamic acid tert-butyl ester
[4-(2-Bromo-phenyl)-butyl]-methyl-carbamic acid tert-butyl ester

Example 7

Synthesis of 2-(2-bromo-5-fluoro-phenyl)-N-methyl-acetamide (Method 9)

Thionyl chloride (9.4 mL, 129 mmol) is added to a solution of (2-bromo-5-fluoro-phenyl)-acetic acid (20.0 g, 85.8 mmol) in dry toluene (400 mL). The mixture is heated at reflux for 4 hours and the solvent is removed in vacuo. The remanence is redissolved in dry toluene (400 mL) and cooled to 0° C. 40% methylamine (aq.) (17.7 mL, 515 mmol) is added dropwise at 0-5° C. The mixture is then stirred at ambient temperature for 16 hours, poured onto water (250 mL) and extracted with ethyl acetate (3×200 mL). The combined organic fractions are washed successively with saturated sodium bicarbonate solution (150 mL) and brine (150 mL), dried (MgSO$_4$) and concentrated in vacuo. This gives 16.2 g (77%) of crystalline 2-(2-bromo-5-fluoro-phenyl)-N-methyl-acetamide.

The following intermediates were prepared analogously:
2-(2-Iodo-phenyl)-N-methyl-acetamide
2-(2-Bromo-5-chloro-phenyl)-N-methyl-acetamide
2-(2-Bromo-4,5-dimethoxy-phenyl)-N-methyl-acetamide
4-(2-Bromo-phenyl)-N-methyl-butyramide

Example 8

Synthesis of [3-(2-bromo-phenyl)-propyl]-methyl-carbamic acid tert-butyl ester (Method 10.)

Methyl amine (8M in ethanol, 38 mL, 304 mmol) is added to 3-(2-bromo-phenyl)-propionaldehyde (6.32 g, 29.7 mmol) and sodium cyanoborohydride (2.24 g, 35.6 mmol) in methanol. The reaction mixture is cooled to 0° C. and acetic acid is added slowly until pH<7. The reaction mixture is stirred for ½ hour and neutralized with aqueous sodium hydroxide. Methanol is removed in vacuo and ethyl acetate and brine are added. The aqueous phase is extracted with ethyl acetate and the combined organic phases are dried with MgSO$_4$ and concentrated in vacuo. The residue is dissolved in THF (150 mL) and di-tert-butyl dicarbonate (7.2 g, 33 mmol) and triethyl amine (5.2 mL, 37.1 mmol) are added. The reaction mixture is stirred for 2 hours, filtered through silica gel and concentrated in vacuo. The residue is purified by flash chromatography (silica gel, ethyl acetate/heptane) to give 3.23 g (33%) of the title compound.

Example 9

Synthesis of 2-[2-(1H-indol-3-ylsulfanyl)-phenyl]-N, N-dimethyl-acetamide (Method 12.)

N,N'-Dicyclohexylcarbodiimide (875 mg, 4.2 mmol) is added to [2-(1H-Indol-3-ylsulfanyl)-phenyl]-acetic acid (600 mg, 2.1 mmol) in 3 mL dry DMF and 7 mL acetonitril and stirred for 10 minutes at room temperature. 5.3 mL dimethyl amine (2M in THF, 10.6 mmol) is added and the reaction mixture is stirred 16 hours at room temperature. The reaction mixture is concentrated in vacuo. The residue is extracted with ethyl acetate (3 times). The combined orgnic phases are washed with brine, dried with $MgSO_4$ and concentrated in vacuo. Purification by flash chromatography on silica gel (ethyl acetate/heptane) gives 116 mg (18%) of the title compound.

The following intermediates were prepared analogously:
2-[2-(1H-Indol-3-ylsulfanyl)-phenyl]-acetamide
2-[2-(1H-Indol-3-ylsulfanyl)-phenyl]-1-morpholin-4-yl-ethanone
2-[2-(1H-Indol-3-ylsulfanyl)-phenyl]-1-thiomorpholin-4-yl-ethanone

Example 10

Synthesis of [2-(1H-indol-3-ylsulfanyl)-phenyl]-acetic acid (Method 13.)

LiOH (1.6 g, 67.3 mmol) is added to [2-(1H-indol-3-ylsulfanyl)-phenyl]-acetic acid methyl ester (2 g, 6.73 mmol) in 27 mL mixture of THF/water (20:7). The reaction mixture is stirred for 10 minutes at 150° C. in a Emrys Optimizer EXP microwave reactor under microwave heating and cooled to room temperature. The reaction mixture is poured into water and acidified with concentrated HCl. Ethyl acetate is added and the organic phase is washed with brine, dried with $MgSO_4$ and concentrated in vacuo to give the title compound, which is used in the next step without further purification.

Example 11

Synthesis of (2-bromo-phenyl)-acetic acid methyl ester (Method 18.)

2 mL $H_2SO_4$ is added to (2-bromo-phenyl)-acetic acid (15 g, 70 mmol) in 150 mL methanol. The reaction mixture is refluxed 16 hours and cooled to room temperature. 100 mL saturated $NaHCO_3$ (aq) is added. Methanol is removed in vacuo. The resulting mixture is extracted with Ethyl acetate. The organic phase is washed with brine, dried with $MgSO_4$ and concentrated in vacuo to give the title compound.

Example 12

Synthesis of 4-(2-bromo-phenyl)-butyric acid

Methanesulfonyl chloride (7.7 mL, 97 mmol) in 100 mL dry THF is added to a solution of 3-(2-bromo-phenyl)-propan-1-ol (17.4 g, 80.9 mmol) and triethyl amine (14.7 g, 146 mmol) in 200 mL dry THF at 0° C. under an argon atmosphere. Water is added and the mixture is extracted with ethyl acetate. The organic phase is washed with brine, dried with $MgSO_4$ and concentrated in vacuo to give 23 g (97%) methanesulfonic acid 3-(2-bromo-phenyl)-propyl ester as an oil. Methanesulfonic acid 3-(2-bromo-phenyl)-propyl ester (23 g, 78 mmol) in 300 mL dry DMF is added to a suspension of potassium cyanide (15.3 g, 235 mmol) in dry DMF. The reaction mixture is stirred at 60° C. for 16 hours. Water is added and the mixture is extracted with ethyl acetate (3 times). The organic phase is washed with brine (twice), dried with $MgSO_4$ and concentrated in vacuo. The residue is placed on a plug of silica gel and eluted with ethyl acetate/heptane (1:4) and concentrated in vacuo to give 16.0 g 4-(2-bromo-phenyl)-butyronitrile (91%) as an oil. 300 mL concentrated HCl is added to 4-(2-bromo-phenyl)-butyronitrile (16.0 g, 71 mmol) in 150 mL acetic acid. The reaction mixture is stirred at 60° C. for 16 hours. The reaction mixture concentrated in vacuo partly and is poured into water. The mixture is extracted with ethyl acetate (3 times). The organic phase is washed with brine (twice), dried with $MgSO_4$ and concentrated in vacuo to give the title compound as a crystalline material.

TABLE 1

Reagents used for the preparation of compounds in Examples 1-10

| Name | Supplier | CAS no. | Cat.no. |
| --- | --- | --- | --- |
| 6-Fluoroindole | Avocado | 399-51-9 | 24633 |
| 5-Fluoroindole | Aldrich | 399-52-0 | F910-8 |
| 4-Fluoroindole | Aldrich | 387-43-9 | 45,739-6 |
| 7-Fluoroindole | Lancaster | 387-44-0 | 17621 |
| 7-Methoxyindole | Aldrich | 3189-22-8 | 11,398-0 |
| 5-Fluoro-2-Methylindole | Aldrich | 399-72-4 | 51,153-6 |
| 5-Chloroindole | Aldrich | 17422-32-1 | C4,760-4 |
| 4-Chloroindole | Biosynth | 25235-85-2 | C4200 |
| 7-Chloroindole | Matrix | 53924-05-3 | 8757 |
| 1-Methylindole | Aldrich | 603-76-9 | 19,398-4 |
| 4-Methoxyindole | Biosynth | 4837-90-5 | M-3450 |
| 5-Aminoindole | | 5192-03-0 | |
| 7-Nitroindole | | 6960-42-5 | |
| 6-(Methylsulfonyl)-1h-Indole | Apollo | NA | OR7793 |
| 4-Methylindole | Acros | 16096-32-5 | 13389-0010 |
| Methylamine | Aldrich | 74-89-5 | 42,646-6 |
| Dimethylamine | Aldrich | 124-40-3 | 39,195-6 |
| Morpholine | Aldrich | 110-91-8 | 25,236-0 |

TABLE 1-continued

Reagents used for the preparation of compounds in Examples 1-10

| Name | Supplier | CAS no. | Cat.no. |
|---|---|---|---|
| Thiomorpholine | Fluka | 123-90-0 | 88885 |
| 2-Iodophenylacetic acid | Aldrich | 18698-96-9 | 53,147-2 |
| 2-Bromo-5-chlorophenylacetic acid | Apollo | 81682-38-4 | OR2153 |
| 2-Bromo-5-fluorophenylacetic acid | Matrix | NA | 11281 |
| 2-Bromo-4,5-dimethoxyphenylacetic acid | Apollo | 4697-62-5 | OR4518 |
| 3-(2-Bromophenyl)propionic acid | Transwld | 15115-58-9 | B3193 |
| 1-Bromo-2-iodobenzene | Aldrich | 583-55-1 | 24,261-6 |
| Allyl alcohol | Aldrich | 107-18-6 | 24,053-2 |
| 3-Buten-1-ol | Aldrich | 627-27-0 | 11,036-1 |
| N-Chlorosuccinimide | Aldrich | 128-09-6 | 10,968-1 |
| Sulfuryl Chloride | Aldrich | 7791-25-5 | 27,850-5 |
| Triisopropylsilanethiol | Aldrich | 156275-96-6 | 42,993-7 |
| Di-tert-butyl dicarbonate | Fluka | 24424-99-5 | 34660 |
| Bis(2-diphenylphosphinophenyl)ether | Aldrich | 166330-10-5 | 51,001-7 |
| Tris(dibenzylideneacetone)dipalladium (0) | Aldrich | 52409-22-0 | 32,877-4 |
| Sodium tert-butoxide | Aldrich | 865-48-5 | 35,927-0 |
| Triethylamine tris(hydrogen fluoride) | Aldrich | 73602-61-6 | 34,464-8 |
| Lithium aluminum hydride | Aldrich | 16853-85-3 | 21,277-6 |
| Aluminum chloride | Aldrich | 7446-70-0 | 29,471-3 |
| N,N'-Dicyclohexylcarbodiimide | Aldrich | 538-75-0 | D8,000-2 |
| 1,1'-Carbonyldiimidazole | Aldrich | 530-62-1 | 11,553-3 |
| Thionyl chloride | Acros | 7719-09-7 | 16949-0010 |

NA: not available

TABLE 2

Measured molecular mass (M + H$^+$), measured HPLC-retention time ($t_R$, min) and UV- and ELSD-purities (%).

| Compound | LC/MS method | $t_R$ min. | UV-purity (%) | ELSD-purity (%) | M + H$^+$ |
|---|---|---|---|---|---|
| 1 | A | 1.87 | 93 | 99 | 301.0 |
| 2 | A | 1.90 | 99 | 99 | 302.1 |
| 3 | A | 1.87 | 98 | 99 | 301.1 |
| 4 | A | 1.80 | 97 | 99 | 301.0 |
| 5 | A | 1.88 | 94 | 100 | 301.1 |
| 6 | A | 1.86 | 92 | 100 | 313.2 |
| 7 | A | 1.92 | 99 | 100 | 315.0 |
| 8 | A | 1.99 | 98 | 100 | 317.1 |
| 9 | A | 1.89 | 100 | 100 | 317.1 |
| 10 | A | 2.01 | 96 | 100 | 317.1 |
| 11 | A | 1.81 | 99 | 100 | 283.2 |
| 12 | A | 2.00 | 99 | 99 | 297.1 |
| 13 | A | 2.00 | 98 | 99 | 317.1 |
| 14 | A | 2.08 | 97 | 98 | 334.9 |
| 15 | A | 2.07 | 95 | 97 | 351.1 |
| 16 | A | 1.96 | 98 | 96 | 318.9 |
| 17 | A | 1.94 | 98 | 98 | 335.1 |
| 18 | A | 1.80 | 97 | 99 | 361.1 |
| 19 | A | 1.83 | 99 | 98 | 377.1 |
| 20 | A | 1.74 | 96 | 99 | 342.9 |
| 21 | B | 1.68 | 100 | 100 | 311.2 |
| 22 | B | 1.62 | 92 | 100 | 341.3 |
| 23 | B | 1.70 | 97 | 100 | 345.2 |
| 24 | B | 1.85 | 97 | 100 | 325.3 |
| 25 | A* | 1.58 | 97 | 100 | 331.2 |
| 26 | A* | 1.47 | 91 | 100 | 327.3 |
| 29 | A** | 0.80 | 98 | 97 | 375.2 |
| 30 | A* | 1.51 | 96 | 100 | 297.3 |
| 31 | A* | 1.60 | 96 | 100 | 315.2 |
| 33 | A* | 1.64 | 95 | 100 | 311.4 |
| 35 | A* | 1.48 | 100 | 98 | 297.2 |
| 36 | A* | 1.48 | 99 | 99 | 339.3 |
| 37 | A* | 1.60 | 85 | 98 | 355.2 |

*same as method A, but with a column temperature of 40° C.,
**same as method A, but but linear gradient elution with 90% eluent A/10% eluent B to 100% eluent B in 2.4 minutes, flow rate is 3.3 mL/minute and the coulumn is Waters SunFire (C18 3.5 μm 4.6 × 30 mm)

Example 13

Transporter Inhibition Assay

Measurements of [$^3$H]-5-HT Uptake into Rat Cortical Synaptosomes

Whole brains from male Wistar rats (125-225 g), excluding cerebellum, are homogenized in 0.40 M sucrose supplemented with 1 mM nialamid with a glass/teflon homogenizer. The homogenate is centrifuged at 1000× g for 10 min at 4° C. The pellet is discarded and the supernatant is centrifuged at 40,000× g for 20 min. The final pellet is homogenized in assay buffer (0.5 mg original tissue/well). Test compounds (or buffer) and 10 nM [$^3$H]-5-HT are added to 96 well plates. Composition of assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 2 g/l glucose and 0,2 g/l ascorbic acid. Buffer is oxygenated with 95% 0$_2$/5% C0$_2$ for 10 min. The incubation is started by adding tissue to a final assay volume of 0.2 mL. After 15 min incubation with radioligand at 37° C., samples are filtered directly on Unifilter GF/C glass fiber filters (soaked for 30 min in 0.1% polyethylenimine) under vacuum and immediately washed with 1×0,2 ml assay buffer. Non-specific uptake is determined using citalopram (10 μM final concentration). Citalopram is included as reference in all experiments as dose-response curve.

Measurements of [$^3$H]noradrenaline Uptake into Rat Cortical Synaptosomes

Fresh occipital-, temporal- and parietal cortex from male Wistar rats (125-225 g) are homogenized in 0.4M sucrose with a glass/teflon homogenizer. The homogenate is centrifuged at 1000× g for 10 min at 4° C. The pellet is discarded and the supernatant is centrifuged at 40,000× g for 20 min. The final pellet is homogenized in this assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 2 g/l glucose and 0,2 g/l ascorbic acid (7,2 mg original tissue/ mL=1 mg/ 140 μl). The buffer is oxygenated with 95% 0$_2$/5% CO$_2$ for 10 min. The pellet is suspended in 140 volumes of assay buffer. Tissue is mixed with test compounds and after 10 min pre-incubation, 10 nM [³H]-noradrenaline is added to a final volume of 0,2 ml and the mixture is incubated for 15 min at 37° C. After 15 mm incubation, samples are filtered directly on Unifilter GF/C glass fiber filters (soaked for 30 min in 0.1% polyethylenimine) under vacuum and immediately washed with 1×0,2 mL assay buffer. Non-specific uptake is determined using talsupram (10 μM final concentration). Duloxetine is included as reference in all experiments as dose-response curve.

Measurements of [³H]Dopamine Uptake into Rat Cortical Synaptosomes

Tissue preparation: male wistar rats (125-250 g) are sacrificed by decapitation and striatum quickly dissected out and placed in ice cold 0,40 M sucrose. The tissue is gently homogenised (glass teflon homogeniser) and the P2 fraction is obtained by centrifugation (1000 g, 10 minutes and 40000 g, 20 minutes, 4° C.) and suspended in 560 volumes of a modified Krebs-Ringer-phosphate buffer, pH 7.4.

Tissue 0,25 mg/well (140 μl) (original tissue) is mixed with test suspension. After 5 minutes pre-incubation at room temperature, 12.5 nM [³H]-dopamine is added and the mixture is incubated for 5 minutes at room temperature. Final volume is 0,2 mL.

The incubation is terminated by filtering the samples under vacuum through Whatman GF/C filters with a wash of 1×0,2 ml buffer. The filters are dried and appropriate scintillation fluid (Optiphase Supermix) is added. After storage for 2 hours in the dark the content of radioactivity is determined by liquid scintillation counting. Uptake is obtained by subtracting the non-specific binding and passive transport measured in the presence of 100 μM of benztropin. For determination of the inhibition of uptake ten concentrations of drugs covering 6 decades are used.

³H-DA=3,4-(ring-2,5,6-³H)dopamine hydrochloride from New England Nuclear, specific activity 30-50 Ci/mmol.

Hyttel, Biochem. Pharmacol. 1978, 27, 1063-1068;
Hyttel, Prog. Neuro-Psychopharmacol. & bil. Psychiat. 1982, 6, 277-295;
Hyttel & Larsen, Acta Pharmacol. Tox. 1985, 56, suppl. 1, 146-153.

The invention claimed is:
1. A compound of the general formula IV:

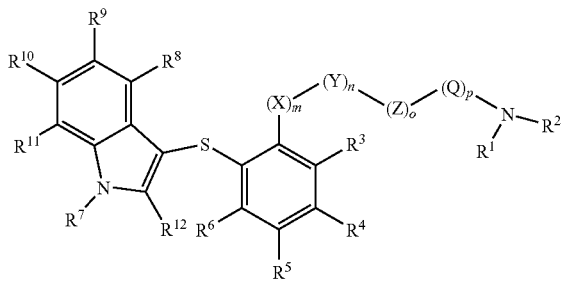

formula IV wherein;
$R^1$-$R^2$ are independently selected from hydrogen, $C_{1-6}$-alk(en/yn)yl, $C_{3-8}$-cycloalk(en)yl, and $C_{3-8}$-cycloalk(en)yl-$C_{1-6}$-alk(en/yn)yl; or $R^1$ and $R^2$ together with the nitrogen form a 4-7 membered ring containing zero or one double bond, optionally said ring in addition to said nitrogen comprises one further heteroatom selected from oxygen and sulphur;

$R^3$-$R^6$ and $R^8$-$R^{12}$ are independently selected from hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl) amino, $C_{1-6}$-alk(en/yn)ylcarbonyl, aminocarbonyl, $C_{1-6}$-alk(en/yn)ylaminocarbonyl, di-($C_{1-6}$-alk(en/yn) yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk (en/yn)ylsulfanyl and $C_{1-6}$-alk(en/yn)ylsulfonyl;

$R^7$ is selected from hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

X is selected from the group consisting of $CH_2$, $CHR^{13}$ or $CR^{14}R^{15}$;

Y is selected from the group consisting of $CH_2$, $CHR^{16}$ and $CR^{17}R^{18}$;

Z is selected from the group consisting of $CH_2$, $CHR^{19}$ and $CR^{20}R^{21}$;

Q is selected from the group consisting of $CH_2$, $CHR^{22}$ and $CR^{23}R^{24}$; and m, n, o and p are independently 0 or 1; wherein m+n+o+p equals 1, 2, 3, or 4, with the proviso that when m+n+o+p equals to 1 then none of X, Y, Z and Q are $CH_2$;

wherein $R^{13}$-$R^{24}$ are independently selected from the group consisting of $C_{1-6}$-alk(en/yn)yl, $C_{3-8}$-cycloalk(en)yl and $C_{3-8}$-cycloalk(en)yl-$C_{1-6}$-alk(en/yn)yl; or a pharmaceutically acceptable salt thereof.

2. The compound according to claim 1, wherein $R^1$ and $R^2$ are independently selected from hydrogen and $C_{1-6}$-alk(en/yn)yl or wherein $R^1$ and $R^2$ together with the nitrogen form a 4-7 membered ring containing zero or one double bond, optionally said ring in addition to said nitrogen comprises one further heteroatom selected from the group consisting of oxygen and sulphur.

3. The compound according to claim 2, wherein $R^3$-$R^6$ and $R^8$-$R^{12}$ are independently selected from the group consisting of hydrogen, halogen, nitro, $C_{1-6}$-alk(en/yn)yl, di-($C_{1-6}$-alk(en/yn)yl)amino, $C_{1-6}$-alk(en/yn)yloxy and $C_{1-6}$-alk(en/yn) ylsulfonyl.

4. The compound according to claim 1, wherein $R^3$-$R^6$ are independently selected from the group consisting of hydrogen, halogen and $C_{1-6}$-alk(en/yn)yloxy.

5. The compound according to claim 1 wherein $R^8$-$R^{12}$ are independently selected from the group consisting of hydrogen, halogen, nitro, $C_{1-6}$-alk(en/yn)yl, di-($C_{1-6}$-alk(en/yn)yl) amino, $C_{1-6}$-alk(en/yn)yloxy and $C_{1-6}$-alk(en/yn)ylsulfonyl.

6. The compound according to claim 1, wherein $R^7$ is selected from the group consisting of hydrogen and $C_{1-6}$-alk (en/yn)yl.

7. The compound according to claim 1, wherein X, Y, Z and Q are $OH_2$.

8. A pharmaceutical composition comprising a compound according to claim 1 and at least one pharmaceutically acceptable carrier or diluent.

9. A method of treating a subject suffering from a disease or disorder comprising administering to the subject a therapeutically effective amount of a compound according to claim 1, wherein the disease or disorder treated is a depressive disorder.

10. The method of claim 9, wherein the depressive disorder is selected from a group consisting of major depressive disorder, postnatal depression, dysthymia, depression associated with bipolar disorder, depression associated with Alzheimer's, depression associated with psychosis and depression associated with Parkinson's.

11. A method of treating a subject suffering from a disease or disorder comprising administering to the subject a therapeutically effective amount of a compound according to claim 1, wherein the disease or disorder treated is an anxiety disorder.

12. The method of claim 11, wherein the anxiety disorder is selected from the group consisting of general anxiety disorder, social anxiety disorder, post traumatic stress disorder, obsessive compulsive disorder, panic disorder, panic attacks, specific phobias, social phobia and agoraphobia.

13. A method of treating a subject suffering from a disease or disorder comprising administering to the subject a therapeutically effective amount of a compound according to claim 1, wherein the disease or disorder treated is a pain disorder.

14. The method of claim 13, wherein the pain disorder is selected from a group consisting of fibromyalgia syndrome, overall pain, back pain, shoulder pain and headache.

15. The method of claim 13, wherein the pain disorder occurs while awake and during daily activities.

16. A method of treating a subject suffering from a disease or disorder comprising administering to the subject a therapeutically effective amount of a compound according to claim 1, wherein the disease or disorder treated is attention deficit hyperactivity disorder.

17. A method of treating a subject suffering from a disease or disorder comprising administering to the subject a therapeutically effective amount of a compound according to claim 1, wherein the disease or disorder treated is stress urinary incontinence.

18. The compound of claim 1, selected from the group consisting of:

{2-[5-Fluoro-2-(1H-indol-3-ylsulfanyl)-phenyl]-ethyl}-methyl-amine;
{2-[2-(6-Fluoro-1H-indol-3-ylsulfanyl)-phenyl]-ethyl}-methyl-amine;
{2-[2-(5-Fluoro-1H-indol-3-ylsulfanyl)-phenyl]-ethyl}-methyl-amine;
{2-[2-(4-Fluoro-1H-indol-3-ylsulfanyl)-phenyl]-ethyl}-methyl-amine;
{2-[2-(7-Fluoro-1H-indol-3-ylsulfanyl)-phenyl]-ethyl}-methyl-amine;
{2-[2-(7-Methoxy-1H-indol-3-ylsulfanyl)-phenyl]-ethyl}-methyl-amine;
{2-[2-(5-Fluoro-2-methyl-1H-indol-3-ylsulfanyl)-phenyl]-ethyl}-methyl-amine;
{2-[2-(5-Chloro-1H-indol-3-ylsulfanyl)-phenyl]-ethyl}-methyl-amine;
{2-[2-(4-Chloro-1H-indol-3-ylsulfanyl)-phenyl]-ethyl}-methyl-amine;
{2-[2-(7-Chloro-1H-indol-3-ylsulfanyl)-phenyl]-ethyl}-methyl-amine;
{2-[2-(1H-Indol-3-ylsulfanyl)-phenyl]-ethyl}-methyl-amine;
{2-[2-(1-Methyl-indol-3-ylsulfanyl)-phenyl]-ethyl}-methyl-amine;
{2-[5-Chloro-2-(1H-indol-3-ylsulfanyl)-phenyl]-ethyl}-methyl-amine;
{2-[5-Chloro-2-(6-fluoro-1H-indol-3-ylsulfanyl)-phenyl]-ethyl}-methyl-amine;
{2-[5-Chloro-2-(4-chloro-1H-indol-3-ylsulfanyl)-phenyl]-ethyl}-methyl-amine;
{2-[5-Fluoro-2-(6-fluoro-1H-indol-3-ylsulfanyl)-phenyl]-ethyl}-methyl-amine;
(2-(2-(4-Chloro-1H-indol-3-ylsulfanyl)-5-fluoro-phenyl)-ethyl)-methyl-amine;
{2-[2-(6-Fluoro-1H-indol-3-ylsulfanyl)-4,5-dimethoxy-phenyl]-ethyl}-methyl-amine;
{2-[2-(4-Chloro-1H-indol-3-ylsulfanyl)-4,5-dimethoxy-phenyl]-ethyl}-methyl-amine;
{2-[2-(1H-Indol-3-ylsulfanyl)-4,5-dimethoxy-phenyl]-ethyl}-methyl-amine;
{4-[2-(1H-Indol-3-ylsulfanyl)-phenyl]-butyl}-methyl-amine;
{4-[2-(4-Methoxy-1H-indol-3-ylsulfanyl)-phenyl]-butyl}-methyl-amine;
{4-[2-(4-Chloro-1H-indol-3-ylsulfanyl)-phenyl]-butyl}-methyl-amine;
Methyl-{4-[2-(1-methyl-1H-indol-3-ylsulfanyl)-phenyl]-butyl}-amine;
{3-[2-(4-Chloro-1H-indol-3-ylsulfanyl)-phenyl]-propyl}-methyl-amine;
{3-[2-(4-Methoxy-1H-indol-3-ylsulfanyl)-phenyl]-propyl}-methyl-amine;
Dimethyl-{3-[2-(3-methylamino-propyl)-phenylsulfanyl]-1H-indol-5-yl}-amine;
Methyl-{3-[2-(7-nitro-1H-indol-3-ylsulfanyl)-phenyl]-propyl}-amine;
{3-[2-(6-Methanesulfonyl-1H-indol-3-ylsulfanyl)-phenyl]-propyl}-methyl-amine;
{3-[2-(1H-Indol-3-ylsulfanyl)-phenyl]-propyl}-methyl-amine;
{3-[2-(6-Fluoro-1H-indol-3-ylsulfanyl)-phenyl]-propyl}-methyl-amine;
Methyl-{3-[2-(1-methyl-1H-indol-3-ylsulfanyl)-phenyl]-propyl}-amine;
Methyl-{3-[2-(5-methyl-1H-indol-3-ylsulfanyl)-phenyl]-propyl}-amine;
2-[2-(1H-Indol-3-ylsulfanyl)-phenyl]-ethylamine;
{2-[2-(1H-Indol-3-ylsulfanyl)-phenyl]-ethyl}-dimethyl-amine;
3-[2-(2-Morpholin-4-yl-ethyl)-phenylsulfanyl]-1H-indole; and
3-[2-(2-Thiomorpholin-4-yl-ethyl)-phenylsulfanyl]-1H-indole;

or a pharmaceutically acceptable salt thereof.

\* \* \* \* \*

UNITED STATES PATENT AND TRADEMARK OFFICE
CERTIFICATE OF CORRECTION

PATENT NO. : 7,629,473 B2  Page 1 of 1
APPLICATION NO. : 11/453022
DATED : December 8, 2009
INVENTOR(S) : Jan Kehler et al.

It is certified that error appears in the above-identified patent and that said Letters Patent is hereby corrected as shown below:

Column 46, line 9, "alk(en/yn)ylsulfonyl, halo-$C_{1-6}$-alk (en/yn)ylsulfanyl" should read --alk(en/yn)ylsulfonyl, halo-$C_{1-6}$-alk(en/yn)ylsulfanyl--.

Column 46, line 51, "Q are $OH_2$." should read --Q are $CH_2$.--.

Column 48, line 5, "{2-[5-Chloro-2-(6-fluoro- 1H-indol-3-ylsulfanyl)-phe-" should read --{2-[5-Chloro-2-(6-fluoro-1H-indol-3-ylsulfanyl)-phe- --.

Column 48, line 7, "{2- [5-Chloro-2-(4-chloro-1H-indol-3-ylsulfanyl)-phe-" should read --{2-[5-Chloro-2-(4-chloro-1H-indol-3-ylsulfanyl)-phe- --.

Signed and Sealed this

Second Day of February, 2010

David J. Kappos
*Director of the United States Patent and Trademark Office*